(12) United States Patent
Cao et al.

(10) Patent No.: US 9,370,304 B2
(45) Date of Patent: Jun. 21, 2016

(54) SUBVOLUME IDENTIFICATION FOR PREDICTION OF TREATMENT OUTCOME

(71) Applicant: THE REGENTS OF THE UNIVERSITY OF MICHIGAN, Ann Arbor, MI (US)

(72) Inventors: Yue Cao, Ann Arbor, MI (US); Peng Wang, Ann Arbor, MI (US); Reza Farjam, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 111 days.

(21) Appl. No.: 13/911,913

(22) Filed: Jun. 6, 2013

(65) Prior Publication Data

US 2013/0329973 A1 Dec. 12, 2013

Related U.S. Application Data

(60) Provisional application No. 61/656,323, filed on Jun. 6, 2012.

(51) Int. Cl.
*G06K 9/00* (2006.01)
*A61B 5/00* (2006.01)
*G06T 7/00* (2006.01)

(52) U.S. Cl.
CPC ............. *A61B 5/0033* (2013.01); *G06T 7/0016* (2013.01); *G06T 2207/10096* (2013.01); *G06T 2207/10104* (2013.01); *G06T 2207/10108* (2013.01); *G06T 2207/20076* (2013.01); *G06T 2207/30016* (2013.01)

(58) Field of Classification Search
CPC ........... G06T 2207/10096; G06T 2207/10104; G06T 2207/10108; G06T 2207/20076; G06T 7/0016; A61B 5/0033
See application file for complete search history.

(56) References Cited

U.S. PATENT DOCUMENTS

| | | | |
|---|---|---|---|
| 2007/0019846 A1* | 1/2007 | Bullitt | G06T 7/0014 382/128 |
| 2007/0081712 A1* | 4/2007 | Huang | G06T 7/0028 382/128 |
| 2007/0274583 A1* | 11/2007 | Sugiyama | G06T 11/008 382/131 |
| 2008/0180664 A1* | 7/2008 | Backman | G01N 21/49 356/317 |

* cited by examiner

*Primary Examiner* — Amara Abdi
(74) *Attorney, Agent, or Firm* — Marshall, Gerstein & Borun LLP

(57) ABSTRACT

Physiological imaging-defined subvolumes of tissues/disease are identified to yield spatially-defined prognostic and/or predictive indicators and/or focal therapy targets within such tissues, in particular tumors, for evaluation over time, for example, prior to and after a therapy treatment. Medical image data is analyzed to delineate subvolumes of tissue based upon multiple physiological, metabolic, and biological imaging properties, where those subvolumes are extracted and analyzed in a probabilistic manner to associate with one or more abnormal or disease phenotype conditions.

20 Claims, 18 Drawing Sheets

SUBVOLUME IDENTIFICATION FOR PREDICTION OF TREATMENT OUTCOME

RELATED APPLICATIONS

This application claims benefit to U.S. Patent Application No. 61/656,323, filed on Jun. 6, 2012, and entitled "SUBVOLUME IDENTIFICATION FOR PREDICTION OF TREATMENT OUTCOME," the entirety of which is hereby incorporated herein by reference for all purposes.

STATEMENT OF GOVERNMENT INTEREST

This invention was made with government support under Contract Nos. RO1 NS064973, R21 CA113699, and 3P01 CA59827 awarded by the National Institutes of Health. The government has certain rights in the invention.

FIELD OF THE INVENTION

The present invention relates generally to a method to identify physiological, metabolic, molecular, and/or biological imaging-defined abnormalities (phenotypes) of diseases for diagnosis, prognosis or prediction of therapy response and/or for intensified local treatment.

BACKGROUND OF THE RELATED ART

When treating tumors, the effectiveness of a treatment is determined by analyzing tumor size, comparing the size pre-treatment and post-treatment. Typically, tumor size is measured through an analysis of magnetic resonance imaging (MRI) or other image data. Such techniques have been used for years and are relatively effective. However, unfortunately, a tumor size change often occurs late, and therefore the patient loses the time window for optimal treatment.

In recent years, physiological, metabolic and molecular imaging has been developed and tested for early prediction of tumor treatment response and outcome with a promise that a biological change in the tumor could occur prior to its size change. Analysis of physiological, metabolic and molecular imaging in the tumor is often done by averaging the values of the relevant physiological imaging parameter in the tumor and then comparing the mean values between pre and post therapy. This is a simple but not effective approach due to neglecting the heterogeneous distribution of the physiological parameter in the tumor, particularly in large tumors. An average value of a physiological imaging parameter in the tumor can wash out the sensitivity of the parameter to a change in the tumor. Indeed, this sensitivity problem is a direct result of the inability of existing techniques to effectively discriminate the information within a tumor image. Tumor image data may reflect numerous different phenotypes/conditions within a tissue mass, but without an ability to properly discriminate between these different phenotypes/conditions, from a medical image data, effective analysis and diagnosis is limited.

A voxel-by-voxel analysis of a change in the physiological, metabolic or molecular imaging parameter of the tumor pre and post therapy is an improvement but requires an accurate registration of a pair of images obtained pre and post therapy. When there is tumor growth and shrinkage from pre to post therapy, the results of the voxel-by-voxel analysis of the physiological imaging are often incorrect or, at a minimum, misleading. The reasons for this are numerous, but the primary culprit is mis-registration of image data at the voxel level. As a tumor changes in size, it is difficult to register with satisfactory certainty a first image of a tumor, taken at one point, e.g., pre-treatment, with the second image of that same tumor, now changed, taken at a second point, e.g., post treatment. This image registration problem commonly requires complex image analysis to correct and still limits the effectiveness of practitioners to use physiological, metabolic and molecular imaging for proper tumor treatment assessment.

To derive a physiological imaging parameter from dynamic contrast enhanced magnetic resonance imaging (DCE-MRI) data or other dynamic PET/SPECT data involves time-consuming pharmacokinetic modeling. Trying to diagnose physiological conditions from that image parameter is prone to error, poor reproducibility and lack of accuracy. For example, in analyzing a physiological imaging parameter of a tumor for therapy response, a parameter such as Gd-DTPA (gadopentetic acid) transfer constant ($K^{trans}$) derived from DCE-MRI by a pharmacokinetic model is sensitive to noise in the DCE-MRI, and has a reproducibility of approximately 20%, which reduces the minimum change that can be detected post therapy compared to pre therapy. Ultimately, medical imaging is used in tumor treatment to determine which treatments are more effective and where to direct those treatments within the patient. For example, intensity-modulated radiotherapy (IMRT) seeks to deliver high-precision nonuniform dose patterns through 'painting' and 'sculpting' doses in a radiation target volume in order to improve the therapeutic ratio and treatment outcome. The conventional IMRT attempts to optimize and deliver a treatment plan having a uniform dose distribution within a target volume delineated primarily based upon anatomic images of computed tomography (CT) and/or MRI. Geometrically conforming high doses within the target volume by IMRT can reduce dose-spread into normal tissue and organs at risk. However, target volume delineation based upon anatomic information provided by CT images and MRI images is limited. Also, considering spatially-heterogeneous biological properties of a tumor, a uniform dose distribution within a target volume might not lead to an optimal treatment outcome.

In any event, voxel-by-voxel image analyses, while effective to an extent, are limiting. A more useful approach is desired.

SUMMARY OF THE INVENTION

The present techniques address the foregoing problems by providing techniques for assessing imaging-defined abnormalities (phenotypes) of diseases in regions of interests, through physiological, metabolic, biologic, and/or molecular imaging, to identify abnormality probabilities of a tumor or other disease, and more specifically multiple biological subvolumes that may be analyzed against any number of disease conditions. In this way, not only are diagnostic determinations possible, but prognostic or predictive determinations can be made for predicting a therapy response and outcome of treatment on an identified subvolume. From here, the techniques may be used to provide a biological-imaging defined target for intensive treatments, e.g., for more effective 'painting' and 'sculpting' of radiation dosage treatments or any number of tumor treatment optimizations.

In some examples, the present techniques are built upon the development of a functional image analysis framework to integrate physiological, metabolic, molecular, and/or biological information from a variety of functional imaging sources, to delineate imaging-defined "phenotype" subvolumes of a tumor and to relate them to treatment response and outcome.

The techniques are designed to delineate subvolumes of a tumor based upon its heterogeneous distributions of physiological, metabolic, and/or biological imaging parameters. For example, the techniques may assign each voxel a probabilistic membership function belonging to the physiological parameter classes defined in a sample of tumors and then calculates the related subvolumes in each tumor. In some examples, the present techniques were used to delineate tumor subvolumes from regional cerebral blood volume (rCBV) and Gd-DTPA (gadopentetic acid) transfer constant ($K^{trans}$) from blood plasma to tissue in patients who have had brain metastases and who received whole brain radiation therapy (WBRT). A subvolume analysis of the tumor, and in particular in changes to the subvolume after starting therapy, was used to assess and predict treatment response from pre-treatment to post-RT. Changes in the rCBV (or $K^{trans}$)-defined subvolumes of the tumors after starting RT were evaluated for differentiating responsive, stable and non-responsive tumors using, from which performance metrics for predicting tumor response to WBRT was developed, with suitable results from Receiver Operating Characteristic (ROC) analysis. The ROC analysis showed that this new metric was significantly better than the decrease in the gross tumor volume (GTV) observed during the same time interval for predicting post-therapy response, suggesting that physiological imaging adds discriminatory information compared to the volumetric change.

Other techniques herein include developing a diffusion abnormality index (DAI) to quantify the extent of abnormality of the tumor apparent diffusion coefficient (ADC) histogram compared to normal tissue. A normal tissue ADC histogram, $H_{NT}$(ADC), is obtained in a normal brain volume of 3-4 cc with the peak normalized to 1. The tumor ADC histogram that usually spreads beyond $H_{NT}$ (ADC) is divided by $H_{NT}$ (ADC) into 3 categories: low (high cellularity), normal, and high (edema and necrosis) ADC. An abnormal diffusion probability function (DAProF) of the tumor is then defined by $1-H_{NT}$(ADC) and band-pass filtered to reduce noise influence at the two tails of the histogram. Given that changes in low and high ADCs could have different roles in response assessment, a factor ($0<\alpha<1$) is used to weight the low ADC contribution to the DAProF related to high ADC's. As a result, a DAI is defined as an integral of the DAProF-weighted tumor ADC histogram. The performance of DAI for predicting the post-treatment radiographic response was also evaluated by Receiver Operating Characteristic analysis and compared with changes in gross tumor volume (GTV) observed during the same time interval. The performance of DAI worsened for the radioresistant lesions treated by WBRT combined with Bortezomib but still better than changes in the GTV, suggesting that the physiological change occurs prior to the volumetric change.

In accordance with an embodiment, a method of analyzing medical image data of a region of interest in a sample tissue, the method comprises: obtaining, at a computer system, the medical image data of the region of interest, the medical image data containing image segments; identifying, at the computer system, one or more candidate physiological, metabolic, molecular and/or biologic parameters that may indicate an abnormal or disease phenotype condition within the region of interest; analyzing, in a subvolume analysis engine, each of the image segments using an algorithm to determine, for each image segment, a probability function for each of the identified one or more candidate physiological, metabolic, and/or biologic parameters; and modeling the image segments, in the subvolume analysis engine, and analyzing the resulting model to identify the abnormal or disease phenotype condition within the region of interest, where the identification produces a diagnostic determination of the region of interest, a prognostic determination of the target tissue, or a predictive determination of the target tissue.

In accordance with another embodiment, an apparatus for analyzing medical image data of a region of interest in a sample tissue, the apparatus comprises: a computer system having a processor executing instructions that, when executed, (i) obtain the medical image data of the region of interest, the medical image data containing image segments, and (ii) identify one or more candidate physiological, metabolic, molecular and/or biologic parameters that may indicate an abnormal or disease phenotype condition within the region of interest; and the computer system further comprising a subvolume analysis engine to (i) analyze each of the image segments using an algorithm to determine, for each image segment, a probability function for each of the identified one or more candidate physiological, metabolic, and/or biologic parameters, (ii) model the image segments, in the subvolume analysis engine, and (iii) analyze the resulting model to identify the abnormal or disease phenotype condition within the region of interest, where the identification produces a diagnostic determination of the region of interest, a prognostic determination of the target tissue, or a predictive determination of the target tissue.

The features, functions, and advantages can be achieved independently in various embodiments of the present invention or may be combined in yet other embodiments.

DESCRIPTION OF DETAILED EXAMPLES

Figure 1A:
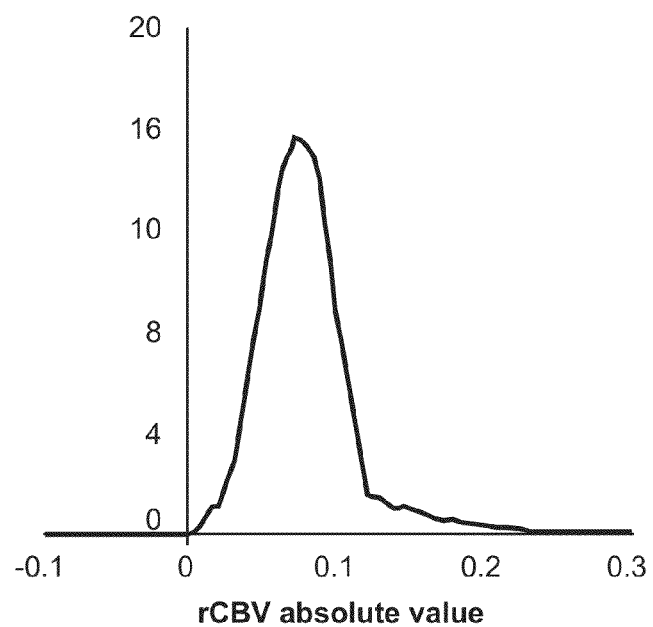
FIG. 1A is a graph that illustrates an example of a Pre-RT rCBV histogram of a typical lesion of brain metastases.

The present techniques provide image analysis of the heterogeneous distribution of one or more candidate physiological, metabolic, molecular and/or biologic imaging parameters in the tumor to determine the abnormality probability map and a quantitative abnormality metric. The abnormality metric and a change during the course of therapy are designed for diagnosis, prognosis and prediction of tumor response to treatment. When assessing a tumor response to treatment, this technique does not require co-registration of images acquired at two different points in time. Furthermore, the techniques do not use hard thresholding to analyze the heterogeneous distribution of the physiological imaging parameters in the tumor. The techniques may be applied to physiological, metabolic, molecular and/or biologic imaging parameters (e.g., vascular parameters or features, cellular parameters or features, etc.) as well as to the dynamic contrast agent/tracer uptake images directly, e.g., DCE-MRI, dynamic PET/SPECT, with or without pharmacokinetic modeling. And the techniques can be used to analyze multiple physiological, metabolic, molecular and/or biologic parameters for testing discriminatory or redundant information, and to combine them into a single metric.

The techniques herein differ from methods that generate parametric response maps (PRMs). In the PRM method, after co-registration of a pair of images acquired at two different time points over therapy, a difference of the image intensities before and after therapy at each voxel is analyzed; and a response value is assigned to each voxel according to its change above or below a cutoff threshold. Although analyzing a voxel-wise change in a tumor is an interesting approach, mis-registration of the image voxels, particularly in the region where a tumor shrinks or grows during the time interval, could compromise the result. The techniques also differ from using a hard threshold to segment the abnormal value of the heterogeneously-distributed physiological imaging parameter. While using a threshold value to segment a tumor volume is simple, the binary decision discards the parameter continuity at the threshold value. Furthermore, finding an adequate threshold value is always a challenge, and often done empirically and sometimes arbitrarily.

The present techniques overcome these challenges, by using a smart algorithm, e.g., fuzzy logic, a genetic algorithm, or Gaussian mixture models, to analyze physiological, metabolic, molecular, and/or biologic imaging-parameters or features of voxels from a sample of tumors. The algorithm may be globally-initiated in a training state from a collective sample and provide localized assessment of individual tumors or regions in an analysis state. A probability density function or histogram of the imaging-parameters or features from all the voxels of the sample of the tumors is created, and analyzed by a fuzzy logic algorithm or other discrimination algorithm for determining the abnormality classifications and related probability functions. For a new tumor, after measuring and deriving the imaging parameters or features, the abnormality classifications determined from the sample of the tumors are applied in order to assign each voxel of the new tumor a probability function of belonging to those image-defined abnormality classes. Then, an abnormality probability map of the tumor can be created as an output for visualization and/or a target for focal therapy, e.g., radiation boost target. Finally, a quantitative abnormality metric of the tumor is created according to its abnormality probability functions for diagnosis and prognosis of the tumor. A change in the abnormality metric during the course of therapy or post therapy, reflecting a change in the physiological, metabolic, molecular or biologic imaging-parameters in the tumor—note such changes often occur before a volumetric change is achieved for prediction of tumor response to therapy. As mentioned before, the present techniques do not depend upon voxel-wise accuracy of registration of a pair of images acquired pre and during or post therapy or use any hard threshold to determine the abnormality level of the tumor.

Figure 10:
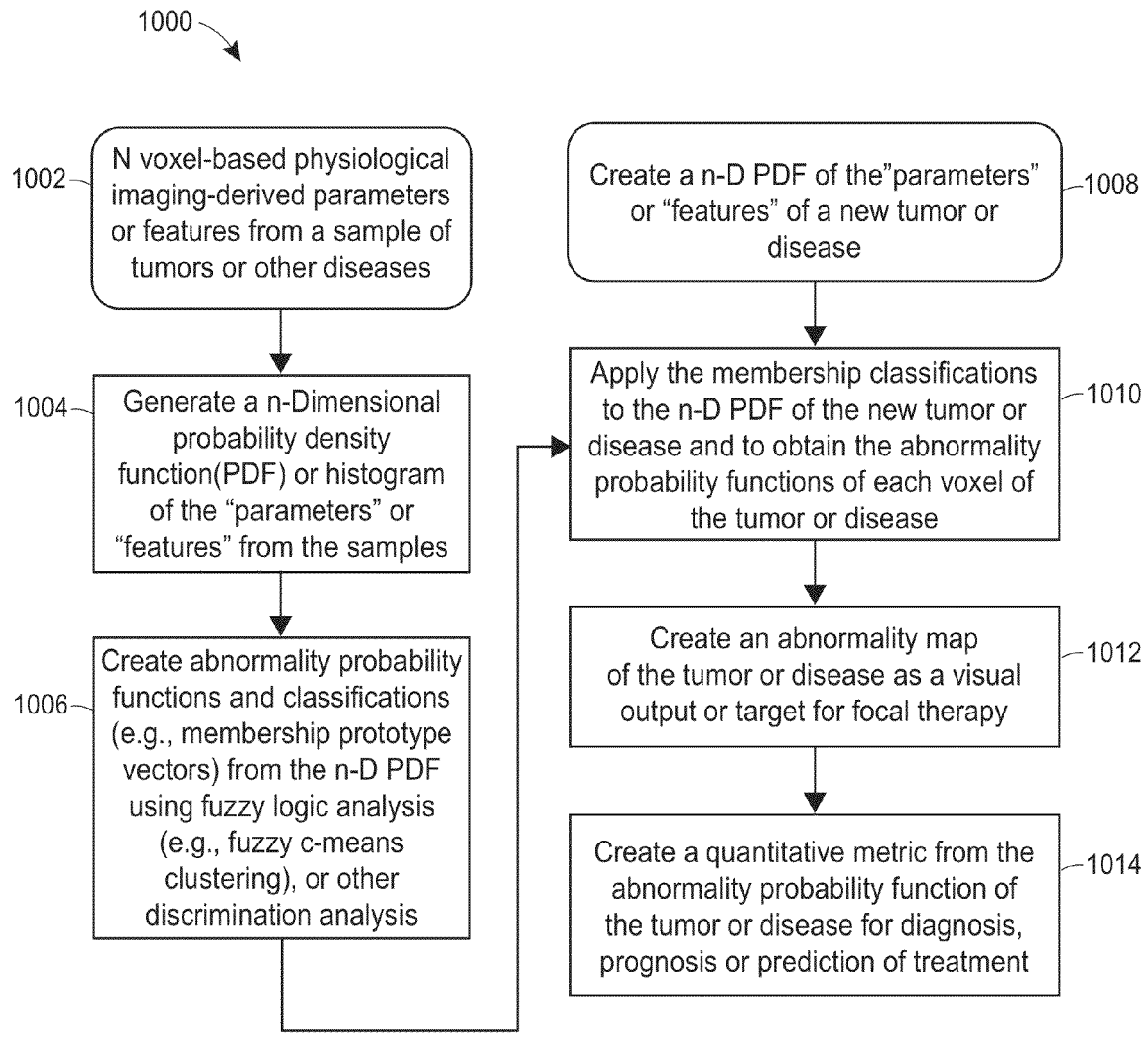
FIG. 10 is a flow diagram of an example method for predicting treatment via subvolume identification.

FIG. 10 illustrates an example implementation of the techniques herein, in particular, used to predict the response of a tumor to radiation therapy. FIG. 10 illustrates an example technique that is based on subvolume analysis of a tumor and identifies N (numbers) of voxel-based physiological imaging-derived parameters or features from a region of interest of a tissue sample that may contain tumors or other diseases. The system generates an n-dimensional probability density function (PDF) or histogram of the parameters or features from the samples. The system then creates an abnormality probability functions and models, such as classifications (e.g., membership prototype vectors) from the n-D PDF using fuzzy logic analysis (e.g., fuzzy c-means clustering), or other discrimination analysis models. The abnormality probability functions and classifications (e.g., the membership classifications) are applied to the n-D PDF of the new tumor or disease to obtain abnormality probability functions of each voxel of the tumor or disease. Then the system creates an abnormality probability map of the tumor or disease as a visual output or target for focal therapy. The system may then, in some examples, create quantitative metrics from the abnormality probability function of the tumor or disease for determining a diagnosis, a prognosis or a prediction of treatment.

The techniques of FIG. 10 may be utilized on different properties of the subvolumes of a tumor, such as the vascularity of subvolumes of the tumor, the cellularity of subvolumes of the tumor, etc. For example, the method may utilize vascular properties, such as blood flow, blood volume, etc. in predicting treatment outcome. On the other hand, the method may also examine cellularity properties (i.e., the water mobility in tissue) to determine an abnormal diffusion coefficient in predicting treatment outcome. The prediction results from the both properties may be combined or added together to provide a more refined, accurate overall prediction for treatment outcome.

Figure 15:
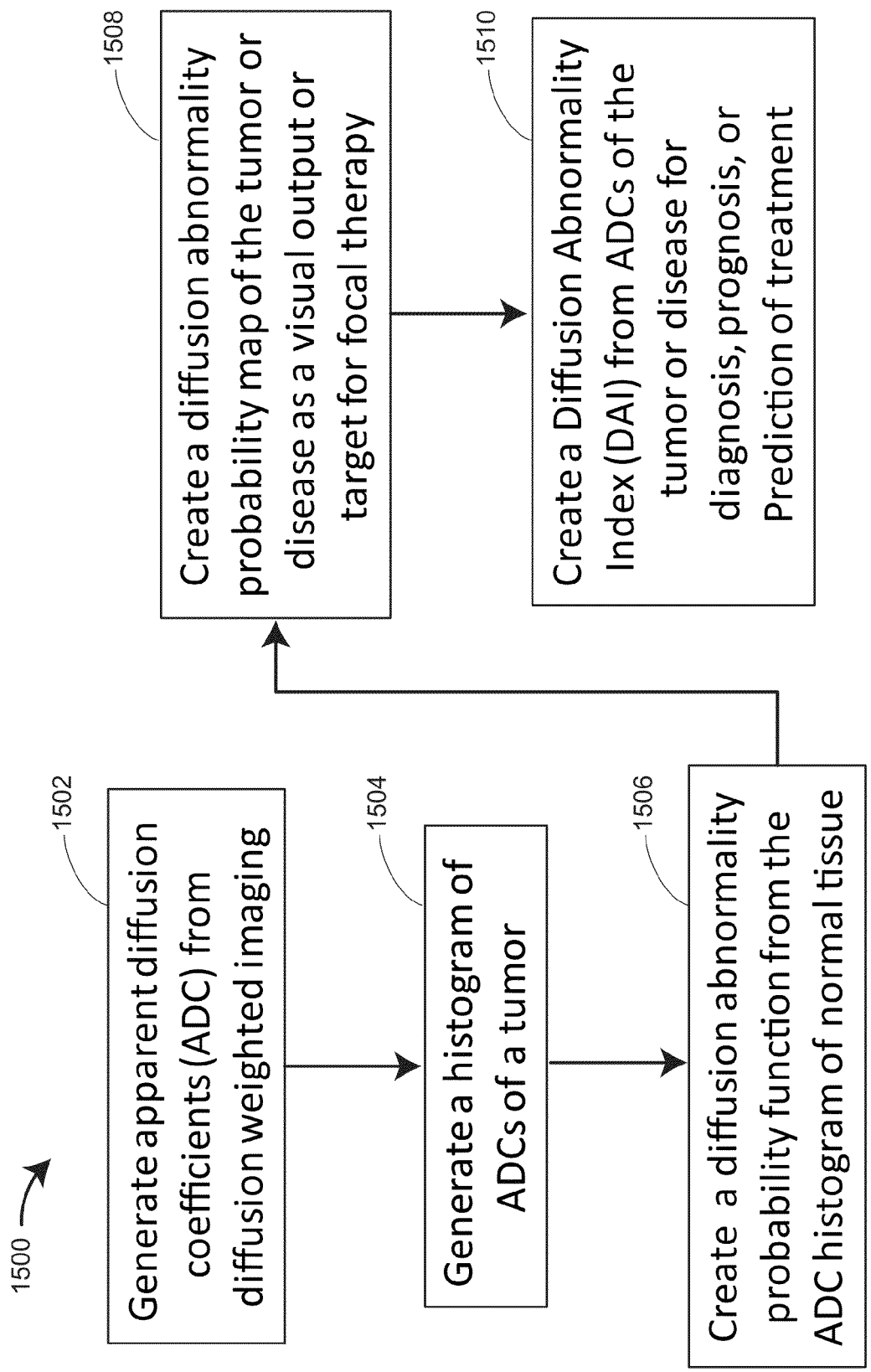
FIG. 15 is a flow diagram of an example method of predicting treatment of a tumor via diffusion abnormality index.

FIG. 15 illustrates an example of another technique herein that also performs an early assessment of a tumor response to radiation therapy. The example in FIG. 15 obtains diffusion weighted-images of tissue (e.g., tissue potentially containing a tumor or diseased tissue region) and generates apparent diffusion coefficients from the images. The system then generates a histogram from the generated apparent diffusion coefficients and also creates a diffusion abnormality probability function from the apparent diffusion coefficient histogram of normal tissue. The system further creates of diffusion abnormality probability map of the identified tumor or diseased tissue region as a visual output or target for focal therapy and generates a DAI from the apparent diffusion coefficients of the tumor or disease for diagnosis, prognosis or prediction of treatment.

I. Subvolume Analysis of a Tumor

The technique of subvolume analysis of a tumor, as illustrated in FIG. 10, is designed to delineate subvolumes of a tumor based upon its heterogeneous distributions of physiological imaging-derived parameters or features. Furthermore, this subvolume analysis method may accept one or more different imaging-derived parameters as inputs. For instance, one of type of physiological imaging-derived parameter may include one or more parameters generated from a pharmacokinetics (PK) modeling technique. Using inputs from this PK modeling technique, the subvolume analysis technique assigns each image voxel a probabilistic membership function belonging to the physiological parameter classes defined in a sample of tumors, and then calculates the related subvolumes in each tumor. Furthermore, this technique may define or model subvolumes of volume-weighted physiological parameters using probabilistic classification of image voxels for features predictive of poor treatment outcome combined with clustering methods, for example.

The subvolume analysis technique of FIG. 10 may also use principal component (PC) features derived from a principal component analysis (PCA) as inputs as opposed to using the PK modeling inputs. This PCA is a pharmacokinetic model free framework that analyzes the dynamic contrast enhanced magnetic resonance imaging (DCE-MRI) data. This PCA technique further utilizes DCE-MRI data from image voxels of a sample of brain tumors to construct a DCE matrix. PCA may then be applied to generate the PCs and subsequent projection coefficient maps. Next, a modeling technique, such as a pattern recognition based upon fuzzy-c-means clustering, may be used to delineate the tumor subvolumes relating to the value of the projection coefficients. The relationship between changes in different tumor subvolumes and treatment response may be evaluated to differentiate responsive from stable and progressive tumors.

A. Pharmacokinetics Modeling in Subvolume Analysis

There is an understanding that high mean or rCBV or $K^{trans}$ in the brain tumor prior to therapy is correlated with a high tumor grade and worse outcome. A reduction in the high rCBV and/or $K^{trans}$ in brain tumors during radiation therapy is associated with better outcome. All these suggest that high-rCBV and/or $K^{trans}$ in the brain tumor, as an imaging-defined tumor "phenotype" and the related changes during therapy, are important prognostic and predictive indictors. Based upon these observations in the brain tumors, the techniques herein were evaluated to delineate the high rCBV (abnormality) probability map of the tumor and/or the abnormality subvolumes defined by rCBV, $K^{trans}$, or combinations of the two parameters in the brain metastases. As discussed above, it was found that the early change in the high rCBV-defined subvolume of the tumor is a better predictor for the post-therapy tumor volumetric change, and has the potential to be used for selecting the lesion and defining the target for intensified treatment. The results also indicated that $K^{trans}$, although a different physiological parameter in the tumor compared to rCBV, does not add significant discriminatory information for assessment of brain metastases response to WBRT. However, the techniques herein can be used to test whether including other physiological imaging parameters in analyses, e.g., apparent diffusion coefficient or 11 C-MET positron emission tomography (PET), fluorodeoxyglucose (FDG) uptake, etc. can improve prediction for treatment response. This type of analysis can help determine whether multiple candidate physiological, metabolic, molecular, and/or biologic imaging parameters provide complementary or redundant information. Also, the analysis can be adapted to specific tumor types and treatment modalities.

Experiment 1

Patient Sample:

In an example implementation of the techniques described herein, twenty patients (11 women and 9 men, ages 41-76 years) diagnosed with brain metastases were enrolled in a prospective MRI study approved by the institutional review board (Table 1). The histology included melanoma (11), non-small cell lung cancer (6), renal cell carcinoma (1), breast cancer (1), and head & neck squamous cell carcinoma (1). All patients received WBRT with a total dose of 30 Gy in 10 fractions (13 patients) or 37.5 Gy in 15 fractions (7 patients). In addition, thirteen patients received Bortezomib during WBRT as a radiation sensitizer. If a patient had three brain metastatic lesions or less, all lesions were included in this analysis. If a patient had more than three lesions, only the three largest lesions were included. If a patient had more than three lesions larger than 1 cm$^3$, the lesions greater than 1 cm$^3$ were also included. As a total, 45 lesions with a median volume of 1.65 cm$^3$ and a range of 0.1-17.6 cm$^3$ were analyzed.

TABLE 1

Patients Characteristics - Example 1

| Pt. No. | Gender/Age (Y) | Histology | No. of lesions | Volume range (cm$^3$) | Total accumulated dose/Fx (Gy) | Concurrent drug treatment |
|---|---|---|---|---|---|---|
| 1 | F/54 | BC | 3 | 4.23-11.78 | 37.5/2.5 | None |
| 2 | M/63 | RCC | 2 | 13.23-14.67 | 30/3 | Bortezomib |

TABLE 1-continued

Patients Characteristics - Example 1

| Pt. No. | Gender/Age (Y) | Histology | No. of lesions | Volume range (cm³) | Total accumulated dose/Fx (Gy) | Concurrent drug treatment |
|---|---|---|---|---|---|---|
| 3 | M/41 | M | 3 | 0.150-1.24 | 37.5/2.5 | Bortezomib |
| 4 | F/60 | NSCLC | 1 | 0.518 | 37.5/2.5 | None |
| 5 | F/52 | M | 1 | 2.74 | 37.5/2.5 | Bortezomib |
| 6 | F/45 | M | 1 | 2.07 | 30/3 | Bortezomib |
| 7 | M/49 | M | 2 | 0.171-4.09 | 30/3 | Bortezomib |
| 8 | F/51 | NSCLC | 3 | 0.503-4.55 | 30/3 | Bortezomib |
| 9 | M/61 | M | 4 | 6.64-17.67 | 37.5/2.5 | Bortezomib |
| 10 | M/52 | NSCLC | 1 | 0.479 | 30/3 | None |
| 11 | F/55 | M | 2 | 0.421-0.545 | 30/3 | Bortezomib |
| 12 | M/76 | M | 1 | 0.680 | 30/3 | Bortezomib |
| 13 | F/46 | M | 6 | 1.25-1.95 | 30/3 | Bortezomib |
| 14 | F/57 | M | 2 | 0.941-1.58 | 30/3 | Bortezomib |
| 15 | F/64 | NSCLC | 1 | 0.108 | 37.5/2.5 | None |
| 16 | M/60 | M | 3 | 0.179-1.31 | 30/3 | Bortezomib |
| 17 | F/74 | M | 4 | 0.690-5.81 | 30/3 | Bortezomib |
| 18 | M/43 | H&N SCC | 1 | 0.601 | 30/3 | None |
| 19 | M/58 | NSCLC | 3 | 2.38-10.69 | 30/3 | None |
| 20 | F/66 | NSCLC | 1 | 0.954 | 37.5/2.5 | None |

Abbreviation:
Pt. No. = patient number;
Y = year;
F = female;
M = male;
BC = breast cancer;
RCC = renal cell carcinoma;
M = melanoma;
NSCLC = non-small cell lung cancer;
and H&N SCC = head and neck squamous cell carcinoma.

Imaging and Data Acquisition:

All patients had MRI scans on a Philips 3T scanner prior to radiation therapy (Pre-RT, where RT is radiation therapy), 2 weeks after the start of RT (2 W), and 1 month after the completion of treatment (1 M Post-RT). MRI scans included pre and post Gd-DTPA volumetric T1 weighted images, multi-slice 2D T2 weighted images, and volumetric dynamic contrast enhanced (DCE) T1 weighted images. The DCE-images were acquired in the sagittal plane with an image matrix of 128×128×80, a field-of-view of 240×240×160 (mm), a voxel size of 2×2×2 (mm³), a flip angle ($\alpha$) of 20°, and TE/TR of 1.04/5.14 msec.

Pre-Processing Image Analysis:

An image registration was used to align the DCE-MRI with the anatomic MRI, both of which were acquired at a same time point—therefore there is no tumor growth or shrinkage. The physician created a tumor volume on the anatomic images, which can be transferred to the DCE-MRI that has a lower spatial resolution. The general Toft model was used to fit DCE-MRI to obtain rCBV and $K^{trans}$ maps with an arterial input function (AIF) determined from a region of interest (ROI) in the carotid artery. Each lesion of interest was manually contoured by a physician on the post-Gd T1 weighed images obtained pre-RT, 2 W and 1 M post-RT. Then, the tumor contours at each time point were transferred to the corresponding rCBV and $K^{trans}$ maps.

Probability Density Functions of Physiological Parameters: to analyze rCBV distributions in the lesions and subsequent changes during treatment, a PDF of rCBV of a lesion was generated by using a non-parametric PDF estimator. The PDF includes 150 evenly-spaced points to cover the range of the rCBV values for all the lesions of interest. A value of the PDF at a point x, H(rCBV=x), of a lesion was calculated as:

$$H(rCBV=x)=n_i: x-\epsilon \leq rCBV_i < x+\epsilon \qquad (1)$$

where $n_i$ was the number of voxels within $|rCBV_{i-x}|<\epsilon$, and $\epsilon$ was a smooth factor of H and set as $$\varepsilon = \frac{\sigma}{4}$$

and where $\sigma$ denotes a standard deviation of the rCBV distribution in the tumor. After calculating Pre-RT and 2 W PDFs for each lesion ($H_{Pre}(x)$ and $H_{2W}(x)$, respectively), $H_{Pre}(x)$ was normalized to have an area under the PDF curve equal to one ($\int H(x)=1$). Then, the normalized $H_{Pre}(x)$s of all the lesions were summed to generate a pooled PDF ($H_p$) of brain metastases, in which each lesion has an equal contribution regardless of its size. An example of H(x) of a lesion is shown in FIG. 1A, and in particular, an example of the Pre-RT rCBV histogram of a typical lesion with a tumor volume of 1.26 cm³. Note that the abnormal tails at both ends of H(x).

Figure 1B:
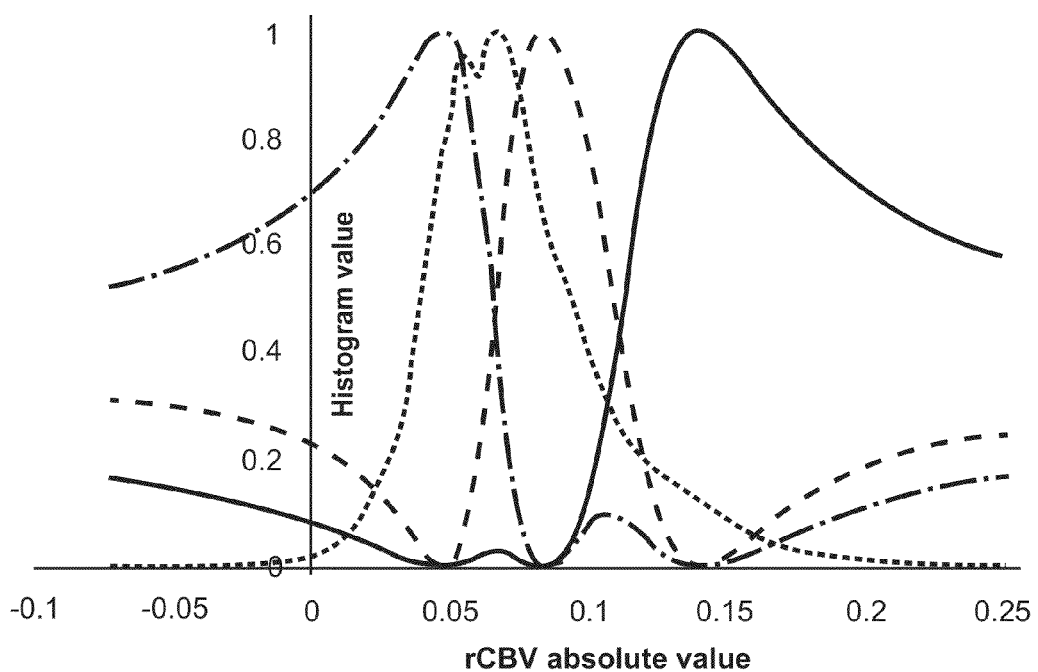
FIG. 1B is a depiction of a graph that illustrates an example of a pooled probability density function of a Pre-RT rCBV from all lesions and three probability membership functions determined by FCM clustering.

Probabilistic Membership Function:

previous studies have suggested that the rCBV distribution of a brain tumor is abnormal compared to normal cerebral tissue. A renormalization of tumor vasculature, such as decreasing the elevated rCBV and increasing the low one, could be an indicator of a tumor response to treatment. The present techniques were used to determine a set of probability functions that are associated with high, intermediate and low rCBV classes. Hence, $H_p(rCBV)$ is partitioned into three classes using fuzzy-c-means (FCM) clustering analysis by minimizing an objective function $J_m$:

$$J_m = \Sigma_{i=1}^{N} \Sigma_{j=1}^{C} P_j(rCBV_i)^m \|rCBV_i - c_j\|^2, \quad 1 \leq m < \infty \qquad (2)$$

where $c_j$ is a prototype vector of the $j_{th}$ class, $P_j(rCBV_i)$ is a probabilistic membership of an rCBV value belonging to the jth class, and m is a fuzzy exponent and chosen as 2. The solutions of Eq. (2) are determined iteratively by:

$$c_j = \frac{\sum_{i=1}^{N} P_j(rCBV_i)^m \cdot rCBV_i}{\sum_{i=1}^{N} P_j(rCBV_i)^m}, \quad (3)$$

$$P_j(rCBV_i) = \frac{1}{\sum_{k=1}^{C} \left[\frac{\|rCBV_i - c_j\|}{\|rCBV_i - c_k\|}\right]^{\frac{2}{m-1}}}. \quad (4)$$

until reaching stopping criteria. Note that the FCM cluster analysis does not classify an rCBV value into a single class (no hard threshold) rather generates a probabilistic function of an rCBV value that belongs to a class. The probabilistic membership function, $P_j(rCBV)$, is a new representation of an rCBV value of a tumor voxel (mathematically transfers the data from an rCBV space into a new space). An example, as shown in FIG. 1B, includes a pooled PDF (light gray) of the Pre-RT rCBV from all the lesions and the three probability membership functions determined by FCM clustering. In this example, the pooled PDF is partitioned into three classes: Representing low (dot-dashed), intermediate (dashed), and high (solid) rCBV classes. A similar computation is applied to $K^{trans}$.

Physiological-Parameter Defined Tumor Subvolume:

a primary interest was to test if a change in a subvolume of the tumor defined by high, intermediate or low rCBV values is related to tumor treatment response. The system defines a subvolume (SV) of a tumor with low, intermediate or high rCBV using the probabilistic membership function $P_j(rCBV)$ and calculated a percentage change in the SV from Pre-RT to two weeks (2 W) as follows:

$$\Delta SV_{Pre \to 2W, i}(rCBV) = \qquad (5)$$

$$\frac{GTV_{2W} \cdot \int P_i(x) \cdot H_{2W}(x)dx - GTV_{Pre} \cdot \int P_i(x) \cdot H_{Pre}(x)dx}{GTV_{Pre-RT} \cdot \int P_i(x) \cdot H_{Pre}(x)dx} \cdot 100,$$

$i \in \{\text{low, intermediate, and high}\}$

A similar calculation was applied to $K^{trans}$.

A percentage change in the gross tumor volume (GTV) from pre-RT to post-RT was used as an endpoint for response assessment. Several patients did not have 3 or 6 months post treatment imaging follow-ups. For the patients in whom 3 and 6 months post-RT images were available, there were good correlations in the GTV changes between 1 and 3 months post RT and between 3 and 6 months post RT (data not shown). Also, previous studies indicated that brain metastases exhibit little pseudo-response and pseudo-progression one month after RT. Therefore, a percentage change was used in the GTV from Pre-RT to 1 month post RT, $\Delta GTV_{Pre \to 1M\,Post-RT}$, as a measure of tumor response to therapy. From Pre-RT to 1 M Post-RT, 16 tumors had a decrease in the GTV at least 25%, defined as responsive, 11 tumors had an increase at least 25%, defined as non-responsive, and the remaining 18 were defined as stable. It was noticed that there were heterogeneous responses of multiple lesions from a single patient. Thus, each lesion was considered independently.

Statistical Analysis:

first, as part of the technique, it was tested if there were any significant differences in the changes of $\Delta SV_{Pre-RT \to 2W, i}(\alpha_i)$ between responsive, stable, and non-responsive tumors using Mann-Whitney U Test. To justify multiple comparisons (e.g., 2, 3 or 6 parameters being simultaneous evaluated), a p-value<0.01 was considered as significant. Next, a Receiver Operating Characteristic (ROC) analysis was performed to evaluate sensitivity and specificity of the significant metrics identified in the previous test for predicting responsive tumors using software package ROCKIT although any ROC software analysis tool may be used, e.g., any of ROCFIT, LABROC4, PROPROC, CORROC, INDROC, ROCKIT and LABMRMC. Also, these newly developed metrics were compared with the conventional ones, including a percentage change in the GTV from Pre-RT to 2 W, $\Delta GTV_{Pre \to 2W}$, and a change in the mean rCBV values of a tumor from pre-RT to 2 W, $\Delta \mu_{Pre \to 2W}(rCBV)$, for predicting post treatment response. The significant difference of the area under ROC curves (AUC) between the metrics were compared by t-test, for which the standard error and the difference between the two AUCs were calculated by the method proposed by DeLong et al.

Finally, it was tested if combining the two physiological parameters of rCBV and $K^{trans}$ could improve prediction for tumor response. To do so, first a joint histogram of the rCBV and $K^{trans}$ of a lesion is computed, e.g., $H(rCBV=x, K^{trans}=y)$. Then, a joint probability function, $P_{i,j}(rCBV, K^{trans}, \alpha)$, is defined as follows:

$$P_{i,j}(rCBV, K^{trans}, \alpha) = \frac{P_i(rCBV) + \alpha \cdot P_j(K^{trans})}{1 + \alpha} \qquad (6)$$

where $\alpha$ is a weighting factor of the two parameters and i and $j \in \{\text{low, intermediate, and high}\}$. Applying the joint probability function to Eq. (5), a percentage change in a subvolume of a tumor defined by rCBV and $K^{trans}$ classes from Pre-RT to 2 W is given by:

$$\Delta SV_{Pre \to 2W, i, j}(rCBV, K^{trans}, \alpha) = \qquad (7)$$

$$\frac{GTV_{2W} \cdot \iint P_{i,j}(x, y, \alpha) \cdot H_{2W}(x, y)dxdy -}{GTV_{Pre} \cdot \iint P_{i,j}(x, y, \alpha) \cdot H_{Pre}(x, y)dxdy} \cdot 100$$
$$\overline{GTV_{Pre} \cdot \iint P_{i,j}(x, y, \alpha) \cdot H_{Pre}(x, y)dxdy}$$

$i \in \{\text{low, intermediate, and high}\}$

The weighting factor $\alpha$ was selected that led to a maximum area under the ROC curve for predicting tumor response.

Figure 2:
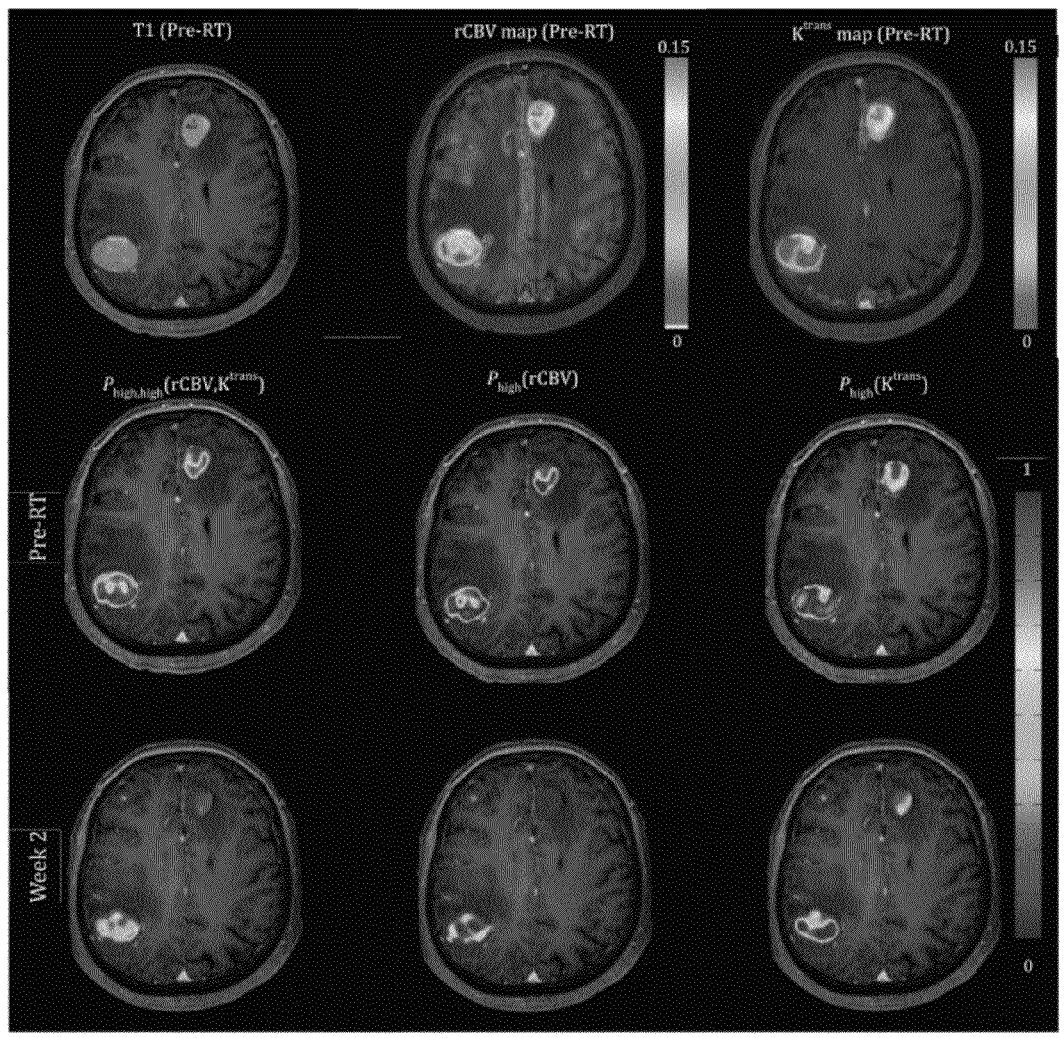
FIG. 2 is a depiction of a graph that illustrates examples of a Pre-RT T1 weighted image, rCBV, and $K^{trans}$ maps of a patient with two brain metastases taken at times relative to radiation therapy.

Probability Function Maps:

examples of maps of the abnormality probability functions belonging to the class of high rCBV, high-$K^{trans}$ and combinations of the two of a responsive and a stable lesion at Pre-RT and at two weeks (2 W) are shown in FIG. 2. In particular, as shown in FIG. 2, the example maps include a T1-weighted (top-left), rCBV (top middle) and Ktrans (top-right). The second row of FIG. 2 includes maps at pre-RT that illustrate the probabilities of voxels belonging to classes with high rCBV (left), high $K^{trans}$ (middle), and high for both rCBV and $K^{trans}$ (right). The third row of FIG. 2 includes maps at end of RT that illustrate the probabilities of voxels belonging to classes with high rCBV (left), high $K^{trans}$ (middle), and high for both rCBV and $K^{trans}$ (right). Note that the spatial distribution of the probability function map of the high rCBV class of a lesion can be different from one of the high $K^{trans}$ class, and both can change from Pre-RT to 2 W. For the responsive lesion, the voxel probability functions belonging to the high rCBV-K$^{trans}$ class were reduced to almost zero from Pre-RT to 2 W, and for the stable lesion the reduction was in a much smaller extent.

Physiological-Parameter Defined Subvolumes:

it was found that the percentage decrease in the high-rCBV subvolumes of the tumors from Pre-RT to 2 W of the responsive group differed significantly from the non-responsive group (p<0.0072) and from a group combining non-responsive and stable tumors (p<0.0057), but marginally from the stable group (p=0.033) (Table 2). Similar but much weaker trends were observed in the percentage decrease in the high-K trans subvolumes of the tumors between the groups. The percentage decrease in the tumor subvolumes defined by both the high rCBV and high K$^{trans}$ classes with an equal weighting from Pre-RT to 2 W differentiated the three groups with improved statistical significances, compared to using either variable alone. Specifically, the responsive group significantly differed from the non-responsive group (p=0.0012) and from the group combining the non-responsive and stable tumors (p=0.0017). For the conventional metrics, the decrease in the mean tumor rCBV from Pre-RT to 2 W of the responsive group differed significantly from the stable group (p<0.0049) and the group of combining the stable and non-responsive tumors (p<0.0066); and the percentage decrease in the GTVs from Pre-RT to 2 W of the responsive group differed significantly from the non-responsive group (p<0.0039) but marginally from the group of combining the non-responsive and stable tumors (p<0.0124).

Figure 4A:
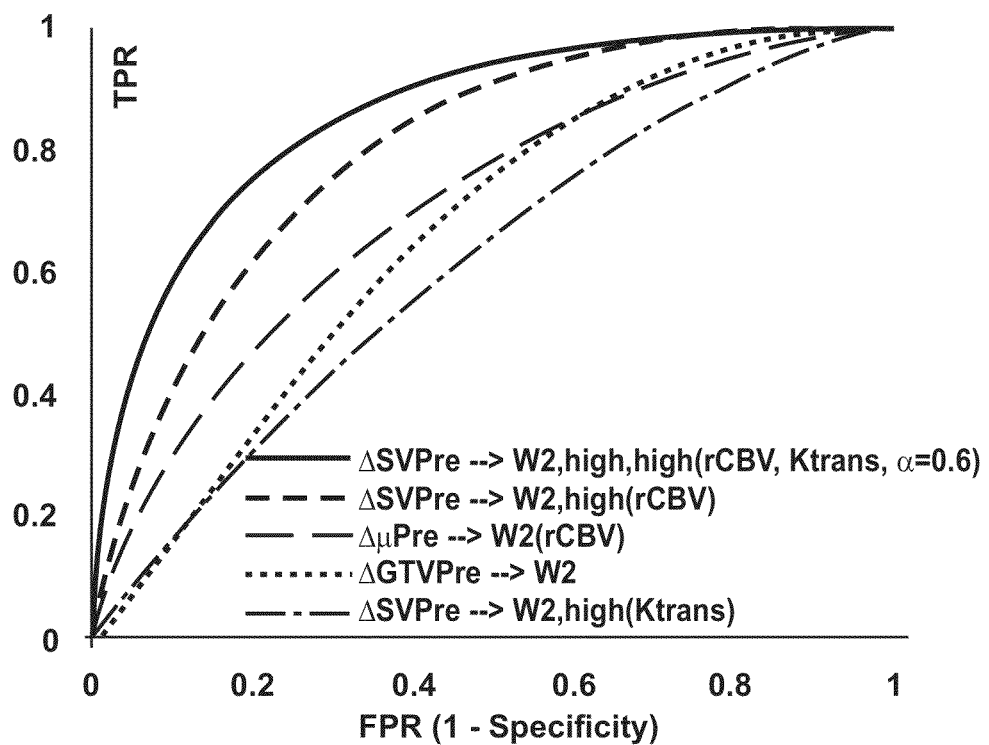
FIG. 4A is a depiction of a graph that illustrates Receiver Operating Characteristic curves of the metrics in Table 2 for predicting responsive tumors.
Figure 4B:
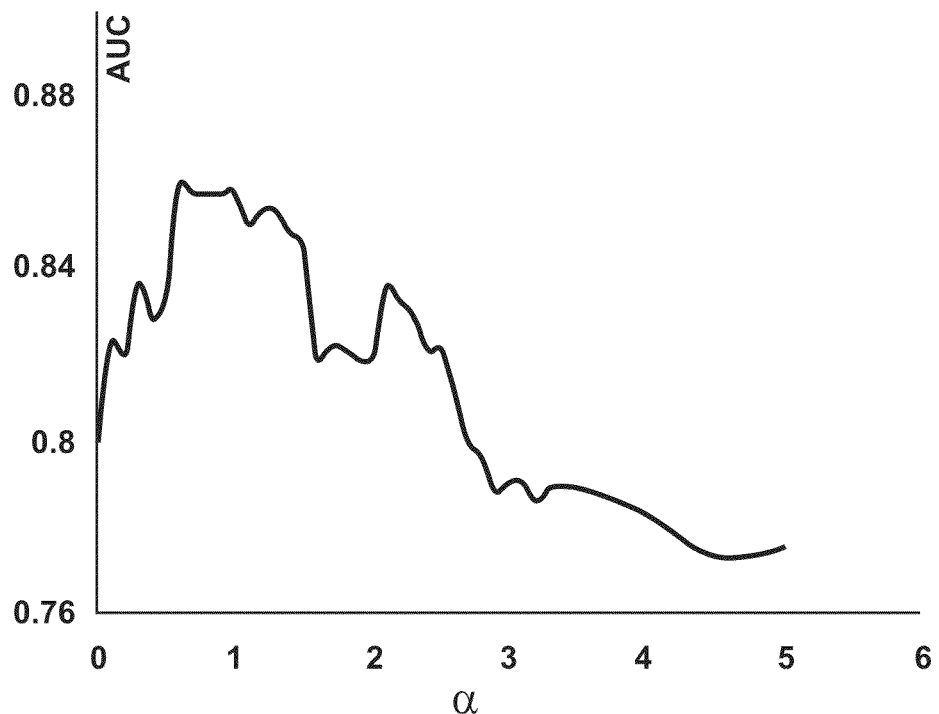
FIG. 4B is a depiction of a graph that illustrates area under the ROC curves vs. a in Equation (7)

Predictive Values of the Physiological Parameter Defined Subvolumes:

the predictive value of the decrease in the subvolumes of the tumors defined by the high rCBV/K$^{trans}$ from Pre-RT to 2 W for predicting responsive tumors post-RT was explored and compared the performance with the two conventional metrics. The ROC analysis showed that the AUCs were 0.80±0.07 (±SEM), 0.70±0.08, 0.67±0.08 and 0.56±0.09 for $\hat{\Delta} SV_{Pre \to 2W,high}(rCBV)$, $\hat{\Delta}\mu_{Pre \to 2W}(rCBV)$, $\hat{\Delta} GTV_{Pre \to 2W}$ and $\hat{\Delta} SV_{Pre \to 2W,high}(K^{trans})$, respectively (as shown in FIG. 4A), indicating the high-rCBV defined subvolume of the tumor had the best performance among the tested variables for predicting responsive tumor. The subvolumes defined by the high-rCBV and high-K$^{trans}$ classes with the weighting factor 0.6, determined by empirical evaluation of the AUCs (as shown in FIG. 4B), resulted in the largest AUC, 0.85±0.06. The statistical analysis of the pair-wise ROC curves revealed that $\hat{\Delta} SV_{Pre \to 2W,high,high}(rCBV,k^{trans},0.6)$ was a predictor slightly but not significantly better than $\hat{\Delta} SV_{Pre \to 2W,high}(rCBV)$ (p>0.18), or $\hat{\Delta}\mu_{Pre \to 2W}(rCBV)$ (p>0.0574). However, both $\hat{\Delta} SV_{Pre \to 2W,high}(rCBV)$ and $\hat{\Delta} SV_{Pre \to 2W,high,high}(rCBV,k^{trans},0.6)$ were predictors significantly better than $\hat{\Delta} GTV_{Pre \to 2W}$ (p=0.022 and p=0.0102, respectively). Finally, the predictive value of $\hat{\Delta}\mu_{Pre \to 2W}$ was slightly but not significantly better than $\hat{\Delta} GTV_{Pre \to 2W}$ (p>0.41).

Thus, the present techniques propose new approaches to delineating the abnormality subvolumes of a tumor defined from physiological, metabolic, and/or biological imaging parameters and relating their early changes to treatment response in the patients who have had brain metastases treated by WBRT. The approaches analyze the heterogeneous distributions of physiological, metabolic, and/or biological imaging parameters of the tumors, then assigns each voxel of the tumor a probabilistic membership function belonging to the various physiological, metabolic, or biological classes defined in a sample of tumors, and finally calculates the related subvolumes in each tumor.

The framework presented herein can be applied to other physiological, metabolic or molecular images, including but not limited to apparent diffusion coefficient and 11 C-Methionion positron emission tomography (PET), to delineate a different physiological-parameter defined subvolume of a tumor. A subvolume of the tumor defined in such way could be a candidate for a radiation boost target volume, for example.

Experiment 2

In another example implementation the present techniques were applied to dynamic contrast enhanced (DCE) MRI image data. The implementation used global initiated regularized local fuzzy clustering (GRELFC), similar to the techniques outlined above, to identify abnormal subvolumes of head and neck cancers (HNC) from heterogeneous distribu-

TABLE 2

Differences between Responsive, Stable, and Non-Responsive Tumors

| | Group of lesions | | | |
|---|---|---|---|---|
| Metric | R vs. S | S vs. NR | R vs. NR | R vs. {S & NR} |
| | | p-value | | |
| $\hat{\Delta} SV_{Pre \to 2W,i}(rCBV)$ i = low | 0.1086 | 0.2517 | 0.6392 | 0.1803 |
| i = intermediate | 0.2771 | 0.3339 | 0.0513 | 0.0990 |
| i = high | 0.0338 | 0.3568 | 0.0072** | 0.0057** |
| $\hat{\Delta} SV_{Pre \to 2W,j}(k^{trans})$ j = low | 0.1012 | 0.8750 | 0.1910 | 0.0773 |
| j = intermediate | 0.3088 | 0.2909 | 0.8243 | 0.5613 |
| j = high | 0.6663 | 0.0162* | 0.0406* | 0.4992 |
| $\hat{\Delta} SV_{Pre \to 2W,high,high}(rCBV, k^{trans}, 1)$ | 0.0218* | 0.0758 | 0.0012** | 0.0017** |
| $\hat{\Delta} SV_{Pre \to 2W,high,high}(rCBV, k^{trans}, 0.6)$ | 0.0199* | 0.0687 | 0.0012** | 0.0015** |
| $\hat{\Delta}\mu_{Pre \to 2W}(rCBV)$ | 0.0049** | 0.2336 | 0.1088 | 0.0066** |
| $\hat{\Delta}\mu_{Pre \to 2W}(k^{trans})$ | 0.5233 | 0.1704 | 0.5704 | 0.8775 |
| $\hat{\Delta} GTV_{Pre \to 2W}$ | 0.1086 | 0.0653 | 0.0039** | 0.0124* |

Abbreviations:
GTV = gross tumor volume;
R = responders;
S = stables;
NR = non-responders;
^The optimum value of α is 0.6, see the results of the ROC analysis
*P < 0.05;
**P < 0.01.

tions of tumor blood volume (BV) and blood flow (BF), i.e., from functional image data for assessment of therapy response.

In operation, BV and BF images, derived from DCE-MRI, of 14 patients with advanced HNC were obtained before chemo-radiation therapy (chemo-RT) and 2 weeks after start of 7-week chemo-RT. The delineated subvolumes of tumors with low BV or BF before and during treatment were evaluated for their associations with local failure. Receiver operating characteristic (ROC) analysis was used to assess performance of the method for prediction of local failure of HNC. As discussed further, the results showed that the sizes of the subvolumes of primary tumors with low BV before and during treatment were significantly greater in the patients with local failure (LF) than with local control (LC) (p=0.02 and 0.01, respectively). While the total tumor volume reductions during treatment were similar for the patients with LF and LC, the reduction rate of the size of the subvolumes of the primary tumor with low BV in response to 2 weeks of chemo-RT was significantly slower for the patients with LF than those with LC. The subvolumes of the tumor with low BV before and during treatment have greater specificity for prediction of local failure, with a given sensitivity, than the pre-treatment total tumor volume, the percentage change in the tumor volume during treatment, or the change in the mean value of BV over the whole tumor during chemo-RT.

Standard care for advanced head-and-neck cancers (HNC) includes aggressive concurrent chemo-radiation therapy (chemo-RT). Intensifying this regimen has resulted in improved control rates as well as increased rates and severity of late toxicity. Despite improvements, failure rates are 20-50% in patients who are negative for human papillomavirus and failures are predominantly local-regional. The present techniques provide a means for prognostic or predictive valuation to facilitate identification of subvolumes of the tumors likely to be resistant to conventional radiation doses in the patients who are at high-risk for local-regional failure and who thus may benefit from intensifying local treatment. Recently, functional imaging that assesses tumor hypoxia or perfusion prior to therapy in HNC has been described. In patients with HNC treated by RT, low tumor perfusion prior to RT and T-stage classification were identified as independent predictors for local failure, suggesting that poorly perfused HN tumors respond poorly to RT, and that pre-RT tumor perfusion provides prognostic value for local control even when accounting for established clinical prognostic factors. Another recent study showed that high pre-therapy tumor blood volume and perfusion were associated with large decreases in tumor volumes in response to induction chemotherapy. By characterizing tumor properties of blood volume (BV) and blood flow (BF) derived from DCE-MRI images, the present techniques showed that an increase of blood volume in the primary tumor volume during the early course of chemo-RT was associated with local control, which indicates that poorly perfused tumors may be resistant to conventional doses of radiation therapy.

In these previous studies, the average BV and BF in the entire tumor volume were investigated for their association with treatment outcome. However, many advanced head-and-neck cancers have quite inhomogeneous perfusion characteristics within the tumor volume, particularly in large tumors. Thus averaging BV and BF values over the entire tumor may not result in optimal parameters for prediction of outcomes. A change in the total tumor volume during the course of chemo-RT, although the total tumor volume in HNC is a clinical prognostic factor, has a poor predictive value for outcomes. The subvolume of the tumor that is resistant to chemo-RT might provide better prediction for outcomes. Therefore, it was hypothesized that the large poorly perfused subvolume of the head-and-neck tumor pre-therapy and persisting during the early course of definitive chemo-RT could be a better indicator for local-regional treatment failure than the tumor size or the average perfusion parameters over the entire tumors.

Identification of Subvolumes of the Tumor:

the technique implemented in this example was designed to globally initiate training to identify fuzzy clusters of the physiological imaging parameters in the feature space, and then classify each tumor volume with local regularization to subvolumes according to the global feature clusters. The technique is designed not only to identify the subvolumes of individual tumors based upon the heterogeneous distributions of physiological imaging parameters but also to be able to compare the classified subvolumes of the tumors across patients and over multiple time points. The fuzzy clustering method, specifically fuzzy C-means clustering (FCM), chosen in the GRELFC method aims to deal with (1) intrinsic variations of the physiological parameters in the tumors, (2) partial volume effects due to the limited resolution of imaging sources, and (3) uncertainty due to noise. FCM clustering is a method of unsupervised learning to assign a set of observations to belong to subsets (clusters) with probability memberships. To partition a set of observations $\{x_k\}$, e.g., image voxels, into c clusters, an objective function with local spatial regularization, $$J_m = \sum_{i=1}^{c} \sum_{k=1}^{N} u_{ik}^m \|x_k - v_i\|^2 + \alpha \sum_{i=1}^{c} \sum_{k=1}^{N} u_{ik}^m \|\bar{x}_k - v_i\|^2 \qquad (8)$$

is to be minimized. In Eq. 8, the first term is a standard FCM cost function and the second term provides a spatial constraint to overcome the effect of image noise and to improve spatial connectivity. Here $u_{ik}$ is a probabilistic (fuzzy) membership of observation xk belonging to class i, $v_i$ is a prototype vector of class i, $x_k$ is a mean or median value of neighbors of voxel k, m defines fuzziness of the membership, and α is a weighting factor of spatial constraints. A 2D or 3D kernel, depending upon image resolution, can be used to define neighbors of each voxel for spatial constraint. Solutions that minimize the objective function of Eq. 8 are given by:

$$u_{ik} = \frac{(\|x_k - v_i\|^2 + \alpha\|\bar{x}_k - v_i\|^2)^{-\frac{1}{(m-1)}}}{\sum_{j=1}^{c}(\|x_k - v_j\|^2 + \alpha\|\bar{x}_k - v_j\|^2)^{-\frac{1}{(m-1)}}} \text{ and} \qquad (9)$$

$$v_i = \frac{\sum_{k=1}^{n} u_{ik}^m (x_k + \alpha \bar{x}_k)}{(1+\alpha)\sum_{k=1}^{n} u_{ik}^m}$$

which are solved iteratively until reaching a stopping criterion. The values for m and α are usually determined empirically. The analysis can be applied to either single- or multiple-component parameters.

In order to evaluate longitudinal changes in physiological imaging parameters of interest in the tumor, a set of data was used as training data to determine definitions of clusters (prototype vectors and relationships between fuzzy memberships and observations), and then the remaining sets of data are partitioned according to the class definitions of training data. To avoid a bias from large tumors in training data, each of the tumor volumes is up-sampled or down-sampled to have an equal number of voxels contributing to the training data while maintaining the initial distribution of the physiological imaging parameters from the original into the re-sampled tumor. To do so, a histogram of the physiological imaging parameters of each tumor is generated, and re-sampled to create a new tumor volume with the same size. The re-created tumor volume, while preserving the original distribution (histogram) of the imaging parameters, cannot maintain the original spatial relationship between voxels, which is not critical for training data to determine prototype vectors of global clusters. To partition individual tumors in the second data set, fuzzy membership of each voxel of each tumor is classified using the prototype vectors found in analysis of the training data by Eq. 9, where spatial constraint is used to improve spatial continuity. Finally, the highest probability of fuzzy membership of each voxel is used to assign the voxel to a discreet class. As a result, the tumor is partitioned into spatial subvolumes based upon the similarity of the physiological parameters of interest. The temporal changes in partitioned subvolumes of the tumor are evaluated for their association with outcomes. To evaluate this method to identify significant subvolumes of the tumor related to outcomes, the method to BV and BF images derived from DCE-MRI of patients with advanced head and neck cancer was applied.

Patients and Treatment:

14 patients with advanced squamous cell carcinomas were enrolled in a prospective MRI study that was approved by the institutional review board at the University of Michigan. Informed consent was obtained from all patients. Table 3 summarized the characteristics of the patients. All patients received definitive 7-week concurrent chemo-RT with a total radiation dose of 70 Gy to the primary gross tumor volume (GTV) and involved nodes, by intensity-modulated radiation therapy (12 patients) or three-dimensional conformal radiation therapy (2 patients). For chemotherapy, 8 patients received carboplatin (1 area under the curve) and paclitaxel 30 mg/m2 weekly; 5 patients received cisplatin 100 mg/m2 once every 3 weeks; and 1 patient received cetuximab with a loading dose of 400 mg/m2 followed by weekly dose of 250 mg/m$^2$.

TABLE 3

Patients Characteristics - Example 2

| Patients | Age(y)/Sex | Disease Location | Stage | MRI Scans Pre/during/3Mpost | Outcome |
|---|---|---|---|---|---|
| 1 | 65/F | Soft palate | T2N3 | y/y/n | LRF/Dead |
| 2 | 62/M | Tonsil | T1 N2a | y/y/y | LRC |
| 3 | 58/M | Hypopharynx | T4 N2b | y/y/y | LF/Dead |
| 4 | 83/M | Larynx | T4N0 | y/y/n | LF/Dead |
| 5 | 61/F | Tonsil | T2N3 | y/y/y | RF |
| 6 | 43/M | BOT + tonsil | T4N2c | y/y/n | LF/Dead |
| 7 | 49/M | Tonsil | T4N2c | y/y/y | LRC |
| 8 | 62/M | BOT | T3N0 | y/y/y | LRC |
| 9 | 39/M | UNP | TxN3 | y/y/y | LRC |
| 10 | 57/M | Nasopharyneal | T2N2b | y/y/y | LRC |
| 11 | 58/M | piriform sinus | T1N2c | y/y/y | LRC |
| 12 | 42/M | Tonsil | T2N2b | y/y/y | LRC/DF |
| 13 | 62/M | Tonsil | T2N2b | y/y/y | LRC |
| 14 | 58/M | Tonsil | T2N2b | y/y/y | LRC |

Abbreviations:
F = female;
M = male;
Pre = pre RT;
during = week 2 during the course of RT;
3Mpost = three months after the completion of RT.
BOT = base of tongue;
UNP = unknown primary disease;
LRF = local-regional failure;
LRC = local-regional control;
LF = local failure;
RF = regional failure;
DF = distant failure.

After receiving chemo-RT, all patients were followed for clinical evaluation. Follow-up visits per protocol took place every 6 weeks for the first two years, then every 3 months for the third year, and every 6 months from the fourth year forward. Per protocol, MRI scans took place 3 months after the completion of RT. FDG positron emission tomography (PET), CT, other MRI scans, or biopsy was elected as clinical indication. The median follow-up time for living patients was 19.6 months (range 14.1 to 36.4 months) post treatment. At these evaluations, 8 patients had local-regional controlled diseases and without distant metastasis, 3 had local failure, 1 had local-regional failure, 1 had regional failure, and 1 had local-regional control but distant failure.

MRI Acquisition:

all MRI scans were acquired using a Philips 3T scanner (Philips Healthcare). Scans were taken before radiation therapy ("pre-RT") and 2 weeks after start of therapy (later referred as "wk-2" or "during-RT"). Each scan included the following series: T1-weighted images, T2-weighted fluid-attenuated inversion recovery (FLAIR) images, DCE T1-weighted images, and post-contrast T1-weighted images. Thirty-two dynamic volumes of T1-weighted MRI were acquired by a 3D gradient echo pulse sequence in the sagittal plane during intravenous injection of 0.1 mL/kg Gd-DTPA with TR/TE=5.1/1.1 ms, flip angle=20 degrees, temporal resolution=7.6 s, and voxel size=2×2×2 mm3 to cover the whole head and neck including primary tumor and involved node.

Gross Tumor Volume (GTV) Definition:

Gross Tumor Volumes (GTVs) were delineated on the post-contrast T1-weighted images acquired pre-RT and during-RT by a head-and-neck radiation oncologist. If available, treatment planning CT and diagnostic PET scans were referenced. The primary and nodal GTVs were drawn separately due to the possibility that the two could respond to therapy differently. Heterogeneous BV and BF of the primary GTV for prediction of local control (LC) or local failure (LF) were investigated.

Quantification of BV and BF:

DCE images were fitted to the modified two-compartment Tofts model. The model assumes the contrast agent concentration Ct(t) in the tissue at time t following the equation below:

$$C_t(t) = K^{trans} \int_0^t e^{-k_{ep}(t-\tau)} C_p(\tau) d\tau + v_p C_p(t) \qquad (10)$$

where Cp(t) is the artery input function, $K^{trans}$ is the volume transfer constant from the plasma to the extravascular extracellular space (EES), $k_{ep}$ is the efflux rate constant from the EES to the plasma, and vp is the fractional volume of the blood plasma. BV is calculated from $v_p$ by $BV=v_p/(1-Hct)$ (Hct is the hematocrit) and converted to per unit mass of the tissue.

BF images were derived by using the method described by Mullani et al. and Hermans et al. described by the following equation:

$$\left(\frac{dC_t(t)}{dt}\right)_{max} = F\rho C_p(t)_{max} \quad (11)$$

where ρ is the density of tissue, F is the blood flow, and $(dCt/dt)_{max}$ is the maximum derivative of the contrast concentration uptake in the tissue.

Figure 5:
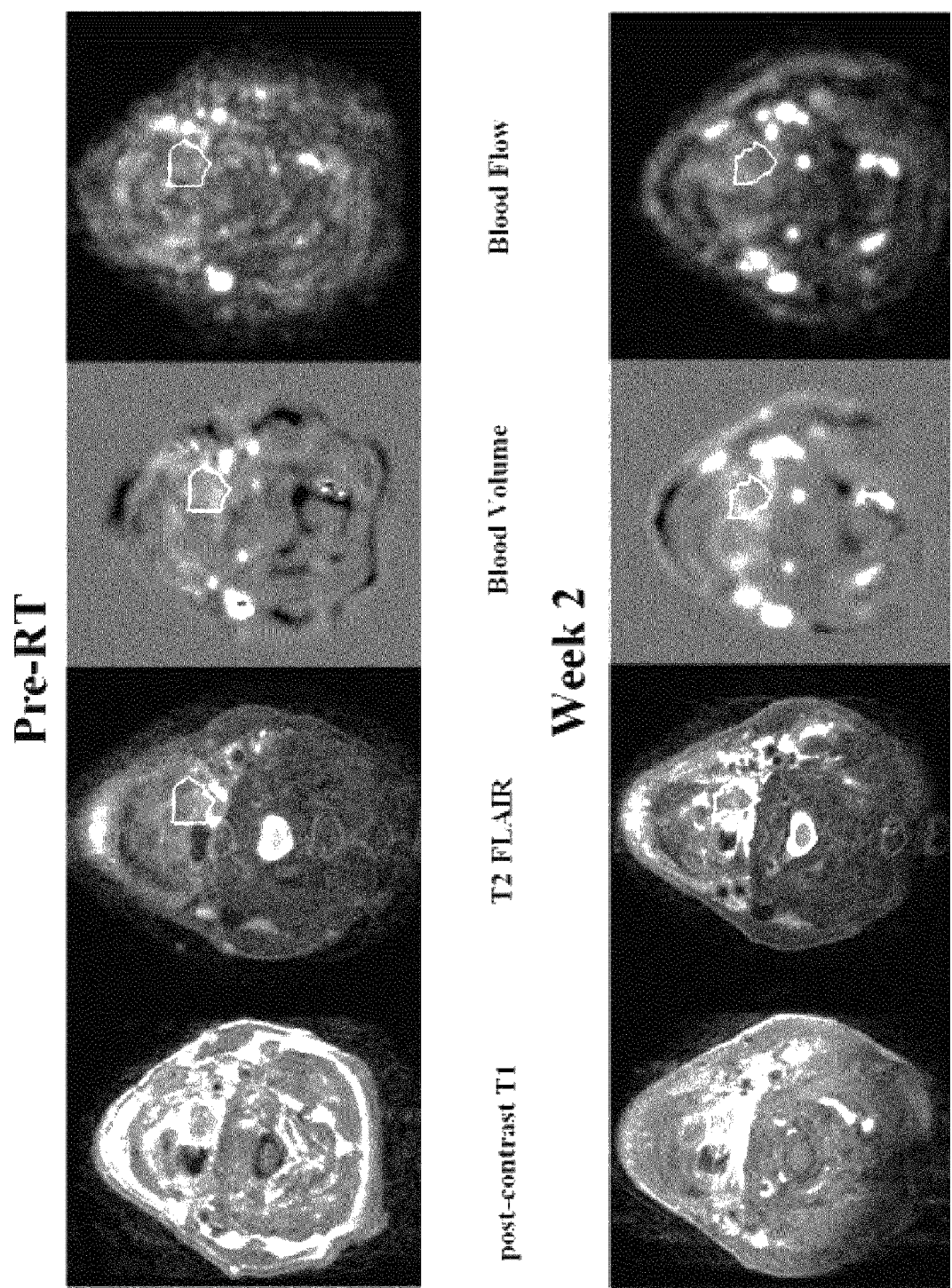
FIG. 5 are images that illustrate examples of a post-contrast TI-weighted MRI, T2 FLAIR, blood volume, and blood flow slices of a patient pre-RT and at week 2.

An example of post-contrast T1, T2 FLAIR, BV, and BF slices is shown in FIG. 5.

Clustering Analyses:

all image analyses were completed using an in-house software package: Functional Image Analysis Tool (FIAT). For analysis of the single parameter of BV, first training data were generated from the pre-treatment BV values of the primary GTVs of all patients. Each of the pre-RT primary GTVs was re-sampled to create 10,000 voxels according to the distribution of BV values within the original GTV. This experience suggested that 10,000 voxels per tumor were sufficient to maintain the distribution of BV in the tumor. As a result, the training data consisted of 100×100×14 voxels (14 is the number of patients), and then was partitioned into 2, 3, or 4 feature clusters using the above described clustering method. The resulting prototype vectors $\{v_i\}$ were adopted to partition each individual GTV before and during therapy to obtain the fuzzy membership of each voxel belonging to the feature classes. The subvolumes of the primary GTVs defined by the clusters with low BV before and during RT were tested for their association with local failure using the Mann-Whitney U test. A two-tailed p-value<0.05 was considered significant. The same analysis was applied to BF data.

Figure 6:
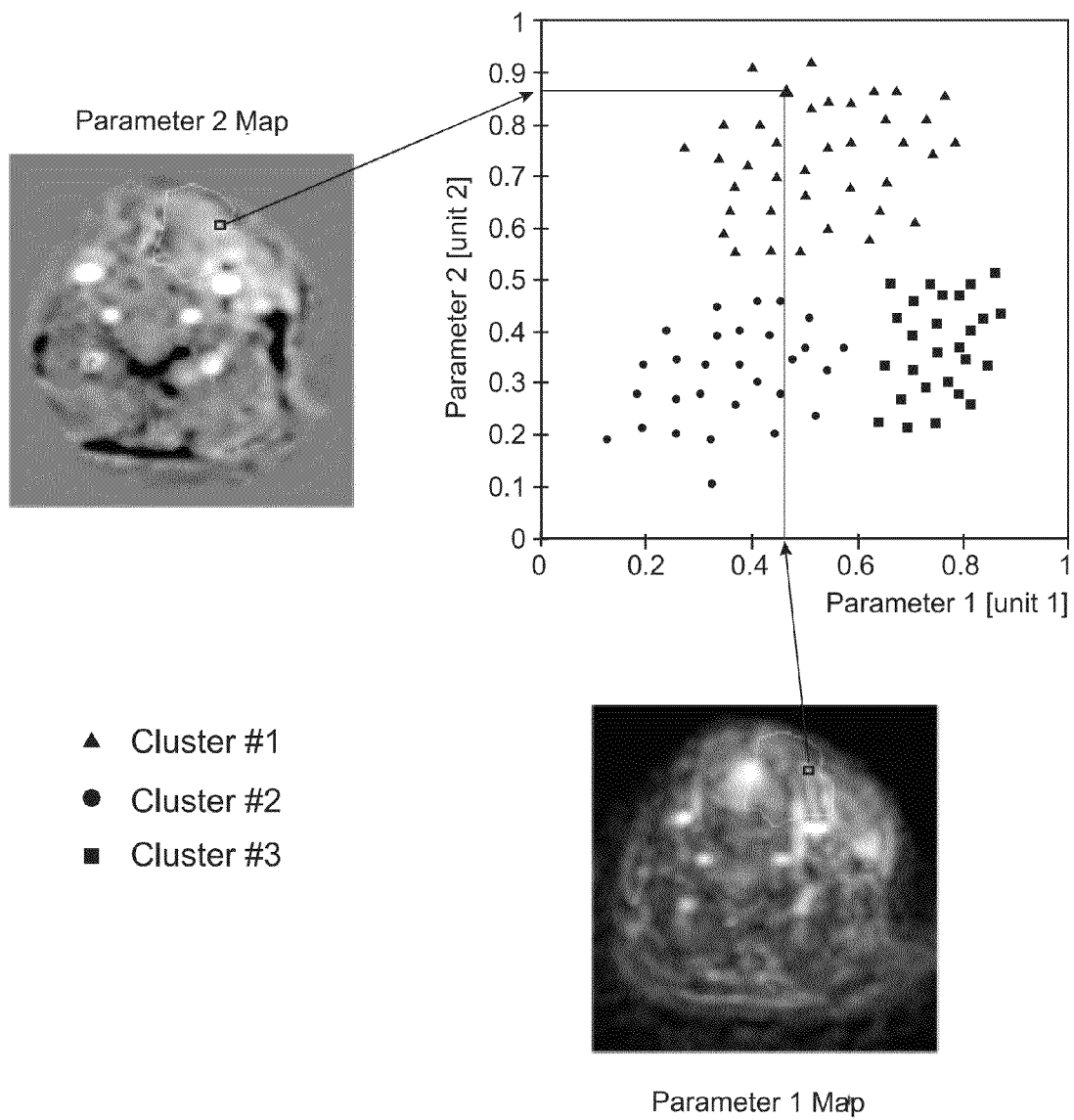
FIG. 6 illustrates the process of classification of the whole gross tumor volume into subvolumes based upon their characteristic physiological features.

To evaluate the discriminatory value of BF combined with BV, $\{x_k\}$ in Eq. 8 was formed to have two components, BV and BF, which were weighted equally for their contributions. The two-component dataset $\{x_k\}$ was analyzed similar to the single parameter. FIG. 6 illustrates the process of classification of the whole GTV into subvolumes based upon their characteristic physiological features and the analysis in the two-component feature space defined by the two parameter maps, BV and BF. The white contour depicts the GTV, and the two-dimensional feature space is depicted with each voxel from the two parameter maps is projected based upon their values. As shown in FIG. 6, the voxels are partitioned into three clusters (e.g., triangles, circles, and squares) using FCM clustering analysis which optimizes homogeneity of the parameters within the cluster and separation between the clusters.

Figure 7A:
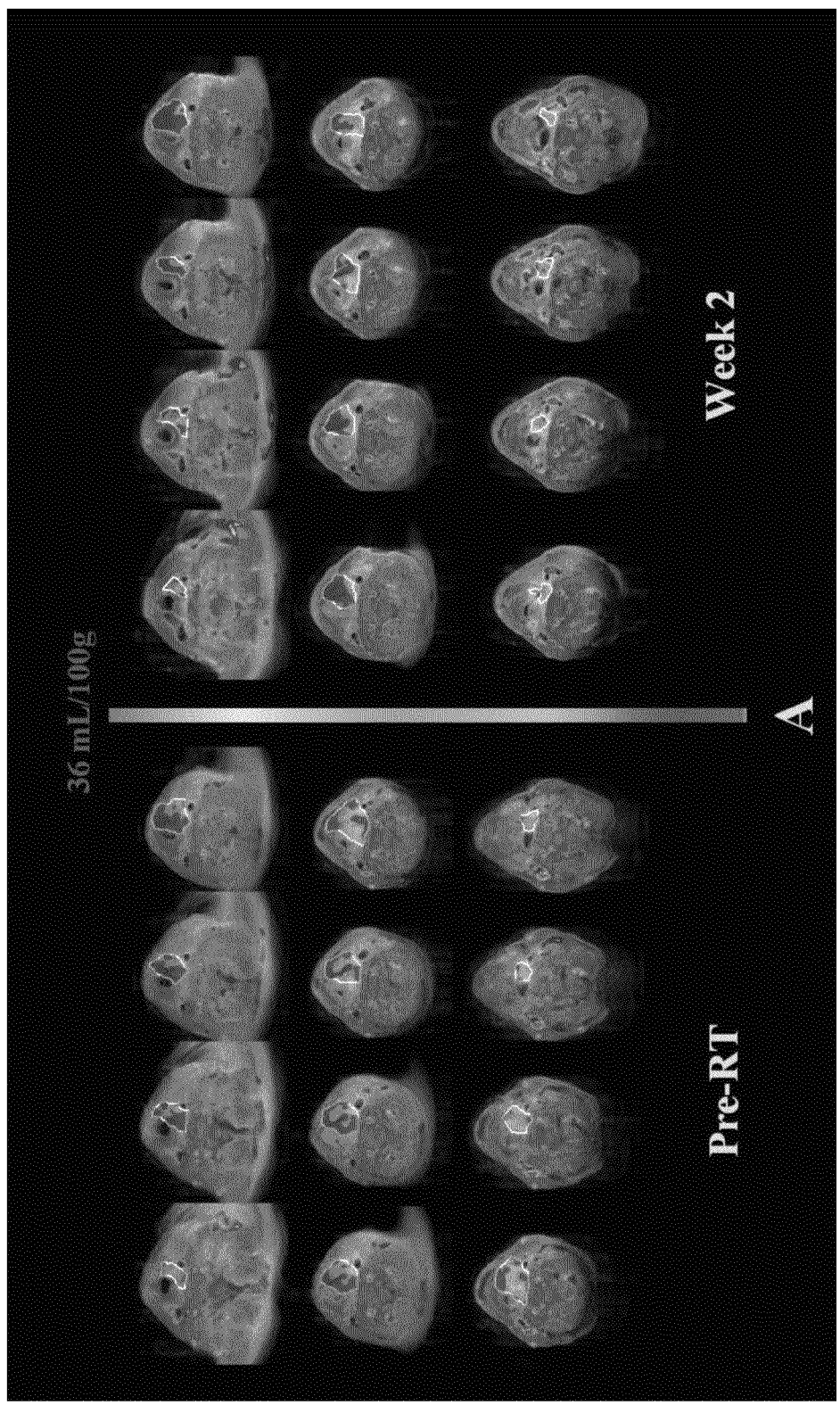
FIG. 7A is an image of a representative example of the subvolumes of the primary gross tumor volume with low blood volume for a local failure case of head and neck cancer.
Figure 7B:
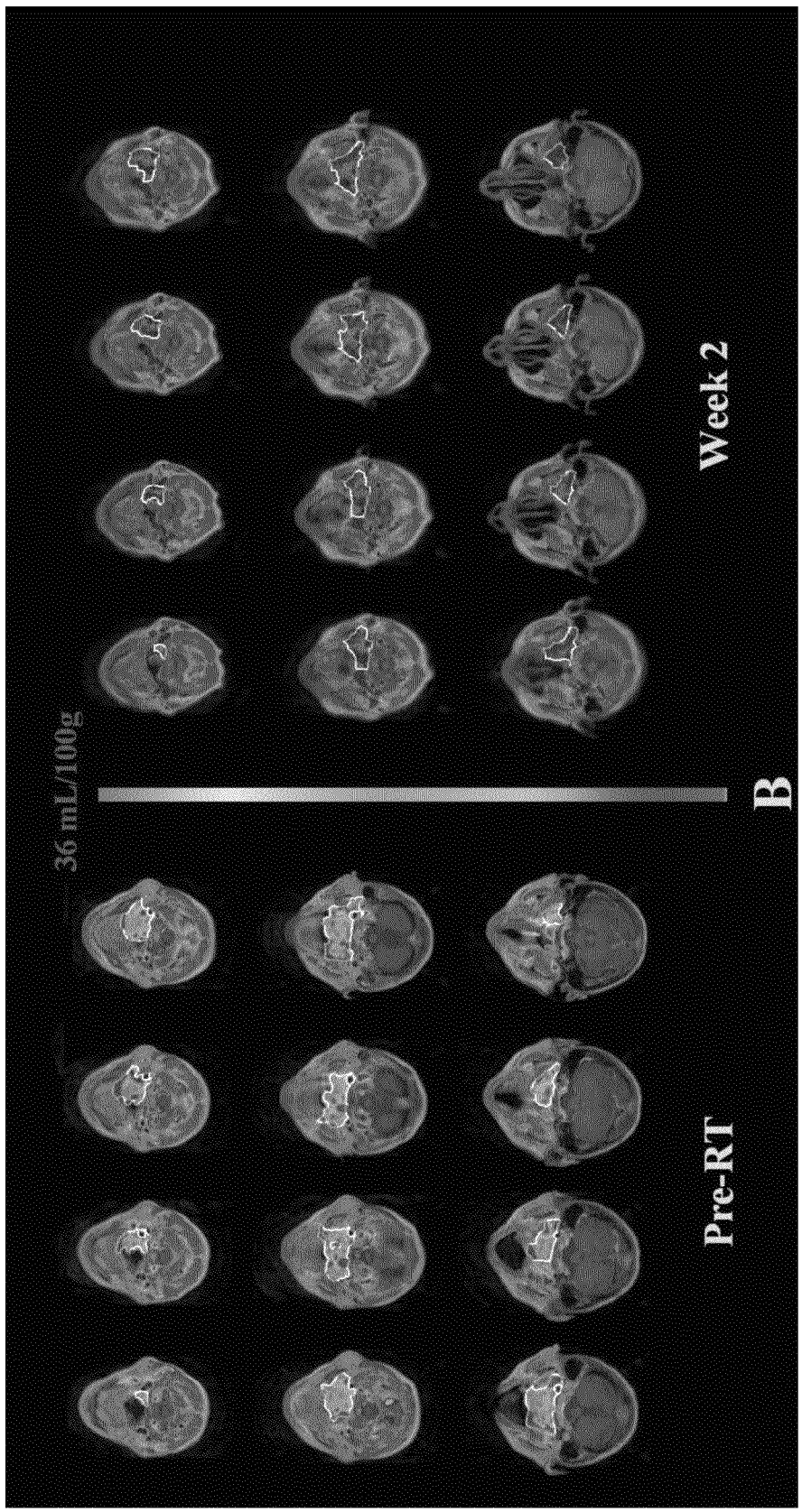
FIG. 7B is an image of a representative example of the subvolumes of the primary gross tumor volume with low blood volume for a local control case of head and neck cancer.

Two representative examples of the subvolumes of the primary GTVs with low BV, pre-RT, and at week 2 are illustrated in FIGS. 7A and 7B. The BV maps are color-coded and overlaid on post-Gd T1-weighted images so that the white contours and blue color represent primary GTV and the subvolumes of the GTV with low BV, respectively. FIG. 7A depicts a local failure case that includes a whole GTV of 61.4 mL and a subvolume of the tumor with low BV of 28.6 mL at pre-RT (left portion of FIG. 7A) and 44.8 mL and 20.9 mL at week 2 (right portion of FIG. 7A), respectively. FIG. 7B depicts a local control case with a whole GTV of 97.5 mL and a subvolume of the tumor with low BV of 16.5 mL at pre-RT (left portion of FIG. 7B) and 52.3 mL and 17.4 mL at week 2 (right portion of FIG. 7B), respectively.

Receiver Operating Characteristic (ROC) Analysis:

to evaluate performance of the subvolumes of the tumors identified from BV, BF or combination of BV and BF for prediction of local failure, receiver operating characteristic (ROC) analysis was performed using software package ROC-KIT. The fitted ROC curves and the areas under the curves (Az) of several representative metrics were generated and compared.

Figure 8:
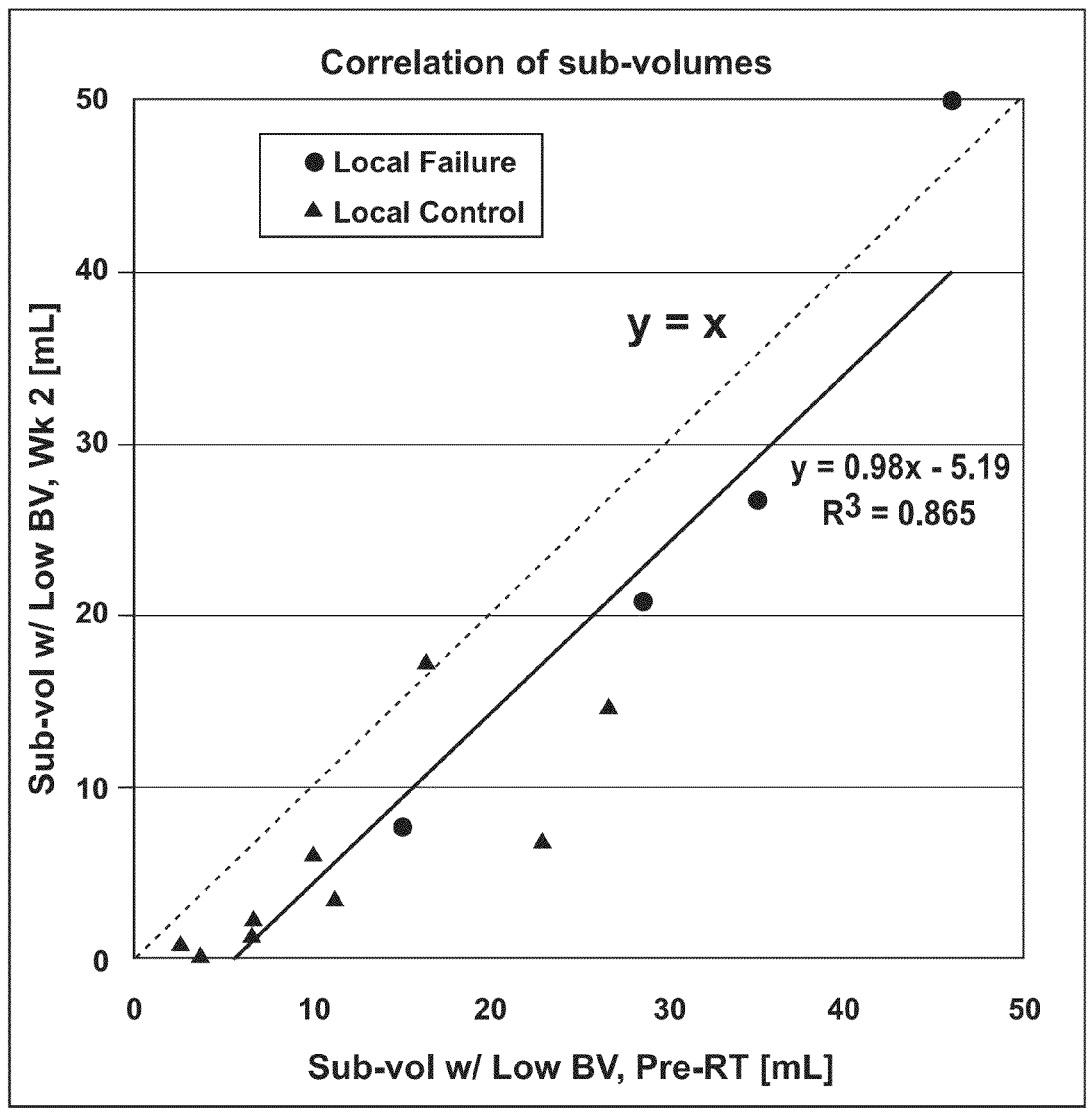
FIG. 8 is a graph that illustrates correlation of subvolumes with low blood volume at the pre-RT and during RT time-points.

Results; Subvolumes of the Primary GTVs with Low BV Pre and During Treatment:

the subvolumes of the primary GTVs derived from clustering analysis of the heterogeneous distribution of BV were assessed and were related to local control (LC) and local failure (LF). When the primary GTVs pre-treatment were partitioned into two classes based upon the BV distribution, the subvolumes of the primary GTVs with low BV in the patients with LC, ranging from 2.4 to 26.6 mL with a median of 9.9 mL, were significantly smaller than those in the patients with LF (p<0.02), from 15.0 to 46.0 mL with a median of 31.9 mL in the patients with LF as shown in Table 4 and in FIG. 8. After receiving 2 weeks of the 7-week chemo-RT treatment course, the subvolumes of the GTVs with low BV decreased to 0.3 to 17.4 mL with a median of 3.7 mL in the patients with LC, and changed to 7.7 to 49.9 mL with a median of 23.8 mL in the patients with LF. The persistence of large subvolumes of the GTVs with low BV during-treatment differentiated LF from LC tumors significantly (p<0.01) (Table 4), suggesting that a large subvolume of poorly perfused tumor both initially prior to therapy and persisting during the early course of chemo-RT may be an indicator for local failure. FIG. 8 depicts the correlation of the subvolumes with low BV at the two time-points (i.e., pre-RT vs. during-RT) and shows that the subvolumes at these two time-points are highly correlated (e.g., p=0.96). As shown in FIG. 8, the scatter plot of the subvolumes of the primary GTVs with low BV pre and during chemo-RT shows that three of the four primary tumors with LF have the largest subvolumes with low BV.

TABLE 4

Summary of Tumor BV and BF Analysis Results

| | Parameters | Median (Range) | | p value |
| --- | --- | --- | --- | --- |
| | | Local Control (n = 9) | Local Failure (n = 4) | |
| BV subvolume | subvolume of tumor with low BV pre-RT [mL] | 9.9 (2.4 to 26.6) | 31.9 (15.0 to 46.0) | 0.02 |
| | subvolume of tumor with low BV wk 2 [mL] | 3.7 (0.3 to 17.4) | 23.8 (7.7 to 49.9) | 0.01 |

TABLE 4-continued

Summary of Tumor BV and BF Analysis Results

| | Parameters | Median (Range) Local Control (n = 9) | Median (Range) Local Failure (n = 4) | p value |
|---|---|---|---|---|
| BF subvolume | subvolume of tumor with low BF pre-RT [mL] | 13.0 (5.2 to 32.1) | 35.5 (17.1 to 67.9) | 0.07 |
| | subvolume of tumor with low BF wk 2 [mL] | 6.3 (0.9 to 21.2) | 20.8 (9.6 to 39.6) | 0.05 |
| BF + BV subvolume | subvolume of tumor with low BV + BF | 10.5 (4.1 to 28.9) | 32.2 (16.3 to 52.9) | 0.03 |
| | subvolume of tumor with low BV + BF | 4.4 (0.4 to 18.6) | 21.6 (8.4 to 45.6) | 0.01 |
| GTV | primary GTV Pre-RT [mL] | 15.8 (5.3 to 97.5) | 74.3 (19.6 to 120.1) | 0.05 |
| | % change in GTV (wk 2 vs. pre-RT) | −27.9 (−65.4 to −11.2) | −21.4 (−44.6 to −8.2) | 0.33 |
| Mean BV | change in mean tumor BV (wk 2 vs. pre-RT) [mL/100 g] | 5.1 (−0.6 to 13.2) | 1.0 (−1.7 to 1.6) | 0.03 |
| Mean BF | change in mean tumor BF (wk 2 vs. pre-RT) [mL/100 g · min] | 20.1 (−3.9 to 54.6) | 15.0 (−22.1 to 41.1) | 0.71 |

All subvolumes above were determined by the analysis for two clusters.

The fractional reduction (or reduction rate) of the subvolumes in the primary GTVs with low BV during-treatment vs. pre-treatment was significantly greater in the patients with LC than those with LF, 56%±9% and 23%±12% respectively ($p<0.05$). In the patients with LF, the initial large subvolumes of the primary GTVs with low BV and slow response rates of the subvolumes to two weeks of chemo-RT suggest that locally intensified treatment is required to further reduction of this persisting and aggressive subvolume of the tumor.

Sub Volumes of the Primary GTVs with Low BF Pre and During Treatment:

it was assessed whether the subvolumes of the primary GTVs identified by the heterogeneous distribution of BF differentiated tumors with LF from LC, either analysis of BF independently or combining BF with BV, to test the discriminatory value of BF in comparison with BV. Analysis of BF alone yielded a similar trend as BV: prior to chemo-285 RT, the patients with LF had large subvolumes of the primary GTVs with low BF (range: 17.1 to 67.9 mL; median: 35.5 mL) while those with LC had small subvolumes with low BF (range: 5.2 to 32.1 mL; median: 13.0 mL). The difference between the two groups was not significant pre-treatment ($p=0.07$). After 2 weeks of treatment, the subvolumes of the primary GTVs with low BF decreased to 9.6 to 39.6 mL with a median of 20.8 mL in the patients with LF and to 0.9 to 21.2 mL with a median of 6.3 mL in the patients with LC, the difference of which was marginally significant ($p=0.05$) (Table 4). While analyzing BF with BV together, there was no improvement in the differentiation of the LF from the LC tumors, compared to analysis of BV alone (Table 4).

Predictive Value of the Subvolumes of the Primary GTVs with Low BV for Local Failure:

the predictive value of the subvolumes of the primary GTVs with low BV pre and during treatment for local failure was explored using ROC analysis, and its performance was compared with other conventional metrics, such as the pre-treatment tumor volume, the percentage change in tumor volume during-treatment, and the change in a mean BV value over the whole tumor during-treatment. The areas under the ROC curves (Az), a measure of overall performance of a metric for prediction of an event (e.g., local failure), indicate that all BV-related (function-based) metrics have better performance than the tumor volume metrics (anatomy-based).

Figure 9:
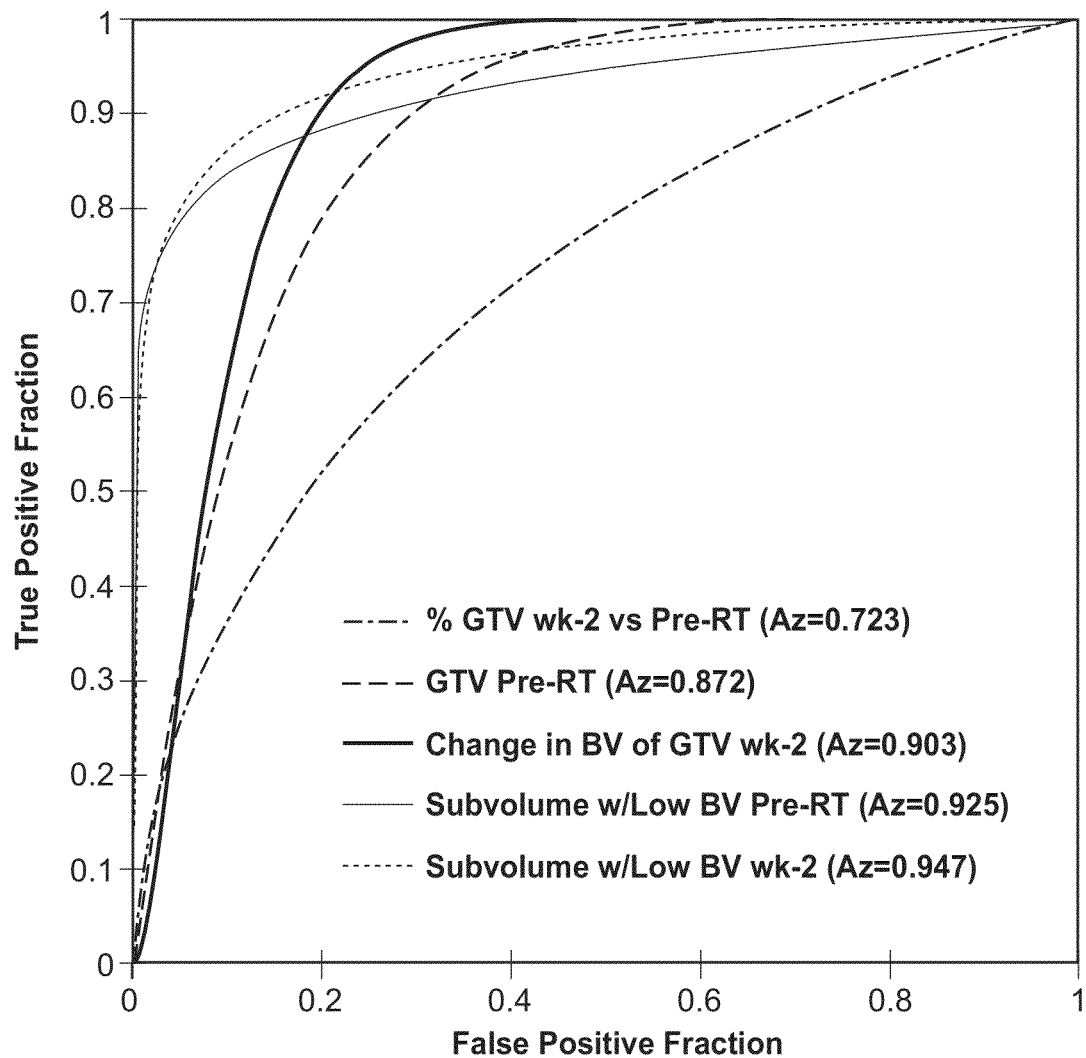
FIG. 9 is a depiction of a graph that illustrates a comparison of fitted Receiver Operating Characteristic curves of five metrics for prediction of local failure of head and neck cancers.

FIG. 9 depicts a comparison of fitted ROC curves of five metrics for prediction of local failure. Specifically, the areas under the ROC curves were 0.872±0.098 for the pre-treatment tumor volume and 0.723±0.158 for the 305 percentage tumor volume change during-treatment. However, the change in the mean of tumor BV values during-treatment, a valuable functional parameter for prediction of local failure reported previously, had an area under the ROC curve 0.903±0.084. When considering the subvolume of the primary GTV with low BV, the areas under the ROC curves increased to 0.925±0.107 for pre-treatment and 0.947±0.079 for during-treatment. The ROC analysis indicates that 85% sensitivity in predicting local failure resulted in 87.5% and 91.0% specificity by the subvolumes of the GTVs with low BV before and during RT, respectively, compared with 83.0% specificity by the change in the mean BV values over the entire GTV during-treatment and 75.5% specificity by the pre-treatment GTV.

Subvolumes of the Nodal GTVs with Low BV:

the subvolumes of the nodal GTVs with low BV were explored. There were two cases with regional failure. Prior to treatment, the subvolumes of the nodal GTVs with low BV were 35.5 and 120.1 mL in the two patients with regional failure, which were greater than those with regional control, ranging from 4.0 to 29.5 mL with a median of 15.6 mL. After 2 weeks of chemo-RT, the subvolumes of the nodal GTVs with low BV changed to 11.6 and 132.5 mL in the patients with regional failure, and to a median of 9.9 mL with a range from 3.3 to 24.5 mL in those with regional control. It is worthwhile to point out that the patient who had local-regional failure had the largest subvolume of the nodal GTV with low BV (~120 mL) and the smallest subvolume of the primary GTV with low BV among the LF cases (~15 mL as shown in FIG. 8), and also the primary and nodal GTVs were anatomically adjacent or connected, which might explain why this case deviated from other local failure cases as shown FIG. 8.

FIG. 10 depicts a flow diagram illustrating an exemplary method for predicting treatment outcome utilizing the vascular properties of a tumor or disease. The method 1000 begins with the system obtaining N-number of voxel-based physiological imaging-derived parameters of a sample of tumors or other diseases (block 1002). Using these samples, the system generates a n-dimensional probability density function or histogram of these parameters of samples (block 1004), and then creates a abnormality probability function from the n-dimensional PDF using fuzzy logic analysis or other discrimination analysis (block 1006). The method 1000 also includes creating a n-dimensional PDF of the parameters of a new tumor or disease (block 1008) and applying the membership classification to the created n-dimensional PDF of the new tumor or disease to obtain the abnormality probability function of each voxel of the tumor or disease (block 1010). The system creates an abnormality probability map of the tumor or disease as a visual output or target or focal therapy (block 1012). The method 1000 includes creating a quantitative metric from the abnormality probability function of the tumor or disease for diagnosis, prognosis, or prediction in treatment (block 1014).

In this example, a method was developed and investigated to identify subvolumes of the tumors by characterizing the heterogeneous tumor blood volume and blood flow before and during treatment using DCE-MRI in patients who had advanced HNC and were treated with concurrent chemo-RT. The subvolumes of the primary GTVs with low BV or BF were related to the outcomes. Also, the predictive value of the subvolumes of the primary GTVs with low BV was explored for local failure and compared these with other quantitative metrics derived from anatomic or functional imaging. It was discovered that the large subvolumes of the primary GTVs with low blood volume pre-treatment and persisting during the early course of chemo-RT are associated with high probability of local failure. For a given sensitivity for prediction of local failure, the tumor subvolume with low blood volume has higher specificity compared to the change in the mean of blood volume values over the whole tumor during-RT, the percentage change of tumor volumes during-RT, or the pre-RT GTV volume. The tumor subvolume with low blood volume might be a better biomarker for identifying the patients with advanced HNC at high-risk for local failure and for defining a radiation boost target to intensify local treatment.

Many large tumors manifest intra-tumor heterogeneity, e.g., multiple phenotypes within a single tumor, which is possibly responsible for heterogeneous treatment response within the tumor. It is plausible that a portion of the tumor is more aggressive or more resistant to treatment, and thereby, might ultimately determine the treatment outcome. However, the mean value or the change in the mean value of a functional imaging parameter over a heterogeneous tumor has generally been used to correlate with treatment outcome in most previous imaging studies, which could compromise the predictive power of the parameter. In this example, in aiming to assess the tumor heterogeneous perfusion and blood volume, and it was found the poorly perfused subvolumes prior to and during chemo-RT have greater specificity for prediction of local failure for a given sensitivity than considering the tumor as a whole (FIG. 8).

It is a challenge to characterize tumor heterogeneity and heterogeneous changes over a longitudinal study. One approach to address the problem is to analyze statistical differences at each voxel over time. This requires a reliable and accurate voxel-to-voxel alignment of images acquired at different time points. The volume, shape and image intensity of the tumors may change over weeks and months. For head-and-neck cancers, the patient position changes due to the neck flexibility over scans can result in additional difficulty for voxel-level image alignment, even with highly sophisticated deformable image registration tools. In addition, voxel-level analyses show large uncertainty and poor reproducibility, which impact on the correlation with response and outcome.

Therefore, in this study, a robust technique (clustering analysis) was developed to characterize heterogeneous vascular and perfusion parameters of head-and-neck tumors as well as their changes over time. This technique can map functional images from different time points into a feature space, and then analyzes the intrinsic properties of the parameter of interest by statistically grouping and splitting the voxels into feature classes (e.g., the voxels with low or high blood volume) based upon their similarities and differences. This technique can be applied to imaging data from longitudinal studies without the requirement of voxel-size accuracy of image registration. The technique can be generalized to other tumors and other imaging parameters. Also, fuzzy clustering used in the method allows the system to manage the continuous distribution of the physiological imaging parameters in the tumor as well as noise in images. Through this work, it was demonstrated that the potential value of the feature class (the subvolume of the tumor with low blood volume) delineated by this method for prediction of outcome and definition of potential radiation boost target volumes.

Several methods have been proposed to automatically segment tumor volumes (binary segmentation) as well as for identification of inhomogeneous tumor subvolumes (multiple classes) from metabolic PET images, e.g., watershed and fuzzy local adapted Bayesian (FLAB) segmentation methods. These methods have focused on how to deal with the influence of object (tumor) size on radioactivity detected by PET due to limited spatial resolution, by iterative segmentation using phantom scans for guidance. Recently, FLAB segmentation has been extended to identify multiple classes in the inhomogeneous FDG distribution in the tumors. However, this method needs to pre-define the fuzzy level, and becomes complicated when dealing with 3 or more classes and various object sizes, especially for small objects (<2 cm). Most importantly, these methods cannot handle the longitudinal data. The questions that these methods attempt to address are generally not major concerns in MRI. In this example, it was discovered that the large poorly perfused subvolume of the HNC both before and during the early course of chemo-RT were associated with local failure. Also, these large subvolumes of tumors with low BV had a slow reduction rate in response to early treatment, suggesting local intensification of treatment may be needed to sufficiently reduce this persisting and aggressive portion of the tumors. Information provided by the early-course scans confirmatively support the findings prior to therapy, which could increase the confidence of clinical decision-making based upon the pre-treatment scans alone. Also, a large reduction in the subvolume of tumor with low blood volume during the early course of chemo-RT could be used as an indicator for a decreased-intensity treatment in the patients who have good outcomes in order to reduce normal tissue toxicity. These findings and reproducibility of test and retest of DCE-MRI without therapy will be further investigated in a large cohort study.

B. Principal Component Analysis in Subvolume Analysis

The subvolume analysis method of FIG. 10 may also use PC features derived from PCA as another input. The PCA may include a pharmacokinetic model free framework that analyzes the DCE-MRI data. This PCA technique may also utilize DCE-MRI data from image voxels of a sample of brain tumors to construct a DCE matrix. PCA is then applied to generate the PCs and subsequent projection coefficient maps. Next, a modeling technique, such as a pattern recognition based upon fuzzy-c-means clustering, may be used to delineate the tumor subvolumes relating to the value of the projection coefficients. The relationship between changes in different tumor subvolumes and treatment response may be evaluated to differentiate responsive from stable and progressive tumors.

This PCA technique may use a general framework to derive a response-predictor from DCE-MRI data without using the PK modeling techniques and a general framework to include a semi-automated or fully automated tool for response assessment and therapy guidance in radiation therapy of brain metastases. In this PCA technique, the system may transfer the DCE curves into an N-dimensional feature space using principle component analysis, may identify the most response-related features using a FCM-based technique, and may combine the features to define the tumor subvolumes.

In some examples, this PCA technique contains two phases: a development phase and a usage phase. In the development phase, a sample of the DCE data from brain metastases is processed and analyzed to develop the model and the predictive metric. In the usage phase, the PCA technique determines if the predictive metric could be extracted rapidly from the DCE data of a new patient scan.

Experiment 3

Using the data gathered from Experiment 1, the following steps of the PCA technique were employed.

Pre-Processing; DCE Curves Normalization:

the dynamic curve at each voxel represents the temporal changes in signal intensity after the contrast injection. The signal intensity change AS from pre (baseline) to post contrast is calculated as following:

$$\Delta S(t) \equiv \frac{s(t) - s_o}{S_o} \quad (12)$$

where S(t) and So represent signal intensities of a DCE curve at times t and 0 (the time of contrast injection), respectively. Note that AS(t) is proportional to AR1, the change in the longitudinal relaxation rate, as long as TR×R1<<1. To account for the individual hemodynamic response to contrast, AS was normalized at each voxel using the peak of the arterial input function, AIFmax, obtained during the same scan as:

$$\Delta S_N(t) = \Delta S(t) \cdot \frac{1}{AIF_{max}} \quad (13)$$

An arterial input function can be determined from a region of interest (ROI) in a large artery (e.g., carotid artery, etc.) manually, semi-automatically or automatically. In the current work, a region of interest containing brain and neck is initially contoured. DCE curves within the contour are averaged to determine the peak enhancement, Tmax, in the tissue. Assuming that the arterial input function reaches the enhancement peak prior to tissue, the first 20 voxels with the maximum enhancement in AS(Tma, −At), one time frame before Tniox, within the contour are thresholded, and then the corresponding DCE curves are averaged to be considered as an arterial input function.

DCE Curve Reconstruction:

the DCE curves in each scan may not be acquired with the exactly same temporal resolutions and time durations. Thus, the DCE curves may be standardized in such a way that all curves have the same temporal resolution and length. The spline curve-fitting method may be used to reconstruct each DCE curve, and resample the curves to have a temporal resolution of 4 sec and a total length of 120 sec, respectively.

DCE Curve Alignment:

the DCE curves from voxels within the tumor volumes of all patients may need to be temporally aligned for further processing. The arterial input function (AIF) obtained from each patient scan may be used to align the DCE curves of voxels in the tumor volumes. The Gamma variate function was fit to each AIF as follows:

$$g = \begin{cases} (t-t_0)^\alpha \exp^{-\beta(t-t_0)} & t \geq t_0 \\ 0 & t < 0 \end{cases} \quad (14)$$

$$AIF = g(t) + \lambda \int_0^t g(t-t')\,dt'$$

All AIFs are then aligned at $t_0$ that is resigned to be time 0. Using the resultant time shifts, the DCE curves from each scan are adjusted accordingly. This process makes all DCE curves aligned based on the start of enhancement in the arterial input function.

Projection Coefficient Map from Karhumen-Loeve Expansion of DCE Curves:

the primary goal is to extract response-predictive features rapidly and directly from the DCE curves. Thus, the DCE curves were expanded using a set of basis functions, by which the coefficients of the projection vectors for each DCE curve is a unique representation in a new space. In the development stage, using DCE data from a sample of brain metastases (e.g., pre-therapy DCE data), the matrix C (N×T) was constructed in which each row represents a DCE curve from one voxel in the tumors. N is the total number of voxels in all tumors and T is the number of time points in each curve. Principal component analysis (PCA) was applied to C to obtain a complete set of a total of T orthonormal principal components ($PC_i$). The Karhumen-Loeve transformation of each DCE curve was performed, $S_N$, in each voxel of the tumor to:

$$\Delta S_N = \Sigma_{i=1}^T a_i PC_i \rightarrow \Delta S_N \equiv (a_1, a_2, \ldots, a_T) \quad (15)$$

where $a_i$ is the projection coefficient (cPC) corresponding to the ith principal component. Each DCE curve in a tumor volume is represented uniquely by $\{\alpha_i\}$ in a T-dimensional coefficient space. However, Eq. (15) can be truncated at the first M principal components which contain 99% of energy of the original DCE curves.

Projection Coefficient Defined Tumor Subvolumes; Probability Density Function of a Projection Coefficient in a Tumor:

each PC depicts a feature of the tumor DCE curve. Each voxel in a tumor has a unique projection coefficient on each PC. For each PC, the projection coefficients of the voxels in a tumor, which can be presented as a volumetric map of a lesion, have a distinct role in predicting the treatment response and outcome. The distribution of the projection coefficients in a large tumor is heterogeneous, similar to the physiological parameters. Similar to what has been done previously for the physiological parameters, the distribution patterns of a projection coefficient, $a_i$, in the lesions were analyzed, and subsequent changes during treatment. A PDF or histogram of $a_i$ of a lesion is generated using a non-parametric PDF estimator. The PDF consists of 150 evenly-spaced points to cover the range of $a_i$ for all the lesions of interest. A value of the PDF at a point x, $H(a_i=x)$, of a lesion is calculated as:

$$H(\alpha_i = x) = n_i: x - \epsilon \leq \alpha_i < x + \epsilon \quad (16)$$

where $n_i$ is the number of voxels within $|\alpha_i - x| < \epsilon$, and $\epsilon$ is a smooth factor of H and set as $\epsilon = \sigma/4$ where $\sigma$ denotes a standard deviation of the $\alpha_i$ distribution in the tumor. For each lesion, PDFs are calculated for scans at baseline (e.g. pre-therapy as $H_{Pre}(x)$) and after starting therapy (e.g. at week-2 during therapy as $H_{2W}(x)$). After $H_{Pre}(x)$ is normalized to have an area under the PDF curve equal to one ($\int H(x)dx=1$), the $H_{Pre}(x)$s of all the lesions are summed to generate a pooled PDF (cPDF), in which each lesion has an equal contribution regardless of its size.

Probabilistic Membership Functions of Projection Coefficients:

Previous studies have suggested that the rCBV (or $K^{trans}$) distribution in a brain tumor is abnormal compared to normal cerebral tissue, as elevated rCBV in a subvolume of the tumor and low rCBV in another one. A renormalization of tumor vasculature, such as decreasing the elevated rCBV and increasing the low one, could be an indicator of a tumor response to treatment. The DCE-derived physiological parameters (e.g., rCBV and $K^{trans}$) and projection coefficients, ($\alpha_1, \alpha_2 \ldots, \alpha_i$), are two representations of the DCE curves. Therefore, it is reasonable to assume that $\alpha_i$ in the brain metastases could also distribute abnormally in contrast to normal tissue, and changes during treatment could predict tumor response to therapy. Hence, similar to what has been done for rCBV previously, the pooled distribution of $H_{pre}(\alpha_i)$ to three classes were classified as high, intermediate and low $\alpha_i$ classes using fuzzy-c-means (FCM) clustering analysis by minimizing the objective function $J_m$:

$$J_m = \sum_{i=1}^{N} \sum_{j=1}^{C} P_j(\alpha_i)^m \|\alpha_i - c_j\|^2, \quad 1 \le m < \infty \qquad (17)$$

where $c_j$ is a prototype vector of the jth class, $P_j(a_i)$ is a probabilistic membership of a $a_i$ value belonging to the jth class, and m is a fuzzy exponent and chosen as 2. The probabilistic membership function, $P_j(a_i)$, describes that a voxel having a projection coefficient $a_i$ has a probability P belonging to a class j, which is a new representation of $a_i$ value of a tumor voxel (mathematically transfers the data from the $a_i$ space into a new space).

Projection Coefficient Defined Tumor Subvolume: the primary interest is to test if a change in a subvolume of the tumor defined by high, intermediate or low $\alpha_i$ values is related to tumor treatment response. The subvolume (SV) of a tumor was defined with low, intermediate or high $\alpha_i$ using the probabilistic membership function $Pj(\alpha_i)$, and calculate a percentage change in the SV from pre-therapy to after starting treatment (eg, 2 weeks) as follows:

$$\hat{\Delta}SV_{Pre \to 2W,j}(\alpha_i) = \frac{GTV_{2W} \cdot \int P_j(\alpha_i) \cdot H_{2W}(\alpha_i) d\alpha_i - GTV_{Pre} \cdot \int P_j(\alpha_i) \cdot H_{Pre}(\alpha_i) d\alpha_i}{GTV_{Pre} \cdot \int P_j(\alpha_i) \cdot H_{Pre}(\alpha_i) d\alpha_i} \cdot 100, \qquad (18)$$

$j \in \{\text{low, intermediate, or high}\}$ where GTV denotes gross tumor volume.

Tumor Subvolume Defined by Combined Projection Coefficients: The overall aim of developing a prediction model for a clinical decision support system is to find a combination of factors that accurately anticipate an individual patient's outcome. Hence, a technique may include combining different cPCs to improve prediction for tumor response compared to using one cPC. To do so, first a joint histogram of $(a_1, a_2 \ldots, a_M)$ of a lesion is computed, e. g. $H(a_1=x1, a_2=x2, \ldots a_M=xM)$. Then, a joint probability function, $P(\{a_i\}, \{\beta_i\})$, is defined as follows:

$$P(\{\alpha_i\}, \{\beta_i\}) = \frac{p_j(\alpha_1) + \sum_{i=z}^{M} \beta_i P_j(\alpha_i)}{1 + \sum_{i=z}^{M} \beta_i}, \beta_1 = 1 \qquad (19)$$

where $\beta_i$ is the weighting factor of each coefficient and $j \in \{\text{low, intermediate, or high}\}$. Applying the joint probability function to Eq. (18), a percentage change in a subvolume of a tumor defined by $\{a_i\}$ classes from pre-therapy to after starting treatment (e.g. 2 weeks (2 W)) is given by:

$$\hat{\Delta}SV_{Pre \to 2W}(\{\alpha_i\}, \{\beta_i\}) = \qquad (20)$$

$$\frac{GTV_{2W} \cdot \int\int \ldots \int P(\{a_i\},\{\beta_i\})H_{2W}(a_1 a_2 \ldots a_M) da_1 \ldots da_M - GTV_{Pre} \cdot \int\int \ldots \int P(\{a_i\},\{B_i\})H_{Pre}(a_1 a_2 \ldots a_M) da_1 \ldots da_M}{GTV_{Pre} \cdot \int\int \ldots \int P(\{a_i\},\{\beta_i\})H_{Pre}(a_1 a_2 \ldots a_M) da_1 da_2 \ldots da_M} \cdot 100$$

The weighting factor $\{\beta_i\}$ is selected based upon the best prediction of response from a developmental dataset and evaluated by an independent data set.

Usage Phase: for a new patient scan, first, pre-processing of the DCE curves was performed and compute the projection coefficient maps of the first M or selected principal components. The histograms or a joint histogram of the selected coefficients were computed within the tumor. Then, using the probability membership function obtained in the development step, the cPC-defined tumor subvolumes were calculated by Eqs. (19) or (20). Finally, a change of the subvolume from pre-therapy to during or post therapy is determined.

Evaluation; Endpoint: a percentage change in the gross tumor volume (GTV) from pre to post RT was used as an endpoint for response assessment. Several patients did not have 3 or 6 months post treatment imaging follow-ups. For the patients in whom 3 and 6 months post-RT images were available, there were good correlations in the GTV changes between 1 and 3 months post RT and between 3 and 6 months post RT. Also, previous studies indicate that brain metastases exhibit little pseudo-response and pseudo-progression one month after RT. Therefore, a percentage change in the GTV from Pre-RT to 1 month post RT was used, $\hat{\Delta}GTV_{Pre \to 1M\ Post-RT}$, as a measure of tumor response to therapy. From Pre-RT to 1 M Post-RT, 16 tumors had a decrease in the GTV at least 25%, defined as responsive, 11 tumors had an increase at least 25%, defined as progressive, and the remaining 18 were defined as stable. It was noticed that there were heterogeneous responses of multiple lesions from a single patient. Thus, each lesion was considered independently.

Parameter Selection and Evaluation: First, the priority of the candidate parameters and subvolumes were ranked by testing if the changes in $\hat{\text{ASV}}_{Pre-RT \to 2W,i}(\alpha_i)$ significantly differentiated responsive tumors from combined stable and progressive ones using Mann-Whitney U Test. Considering M principal components and two independent subvolumes (only two of the three are independent) for each component, a p-value<(0.05/2 M) with Bonferroni correction was considered as a significant cutoff to select the parameters. The conventional metrics, such as a percentage change in the GTV from Pre-RT to 2 W ($\hat{\Delta}\text{GTV}_{Pre \to 2W}$) and a change in the mean rCBV values of a tumor from pre-RT to 2 W ($\hat{\Delta}\mu_{Pre \to 2W}$ (rCBV)), were not considered as the candidate parameters in the model, and thus not used for multiple comparison justification. Next, univariate analysis was performed to evaluate sensitivity and specificity of the selected significant metrics identified in the previous test for predicting responsive tumors using Receiver Operating Characteristic analysis (software package ROCKIT). Also, these newly developed metrics were compared with the conventional metrics including a percentage change in the GTV from Pre-RT to 2 W, $\hat{\Delta}\text{GTV}_{Pre \to 2W}$, and a change in the mean rCBV values of a tumor from pre-RT to 2 W, $\hat{\Delta}\mu_{Pre \to 2W}$(rCBV), for predicting post treatment response. The significant difference of the area under ROC curves (AUC) between the metrics were compared by t-test, for which the standard error and the difference between the two AUCs were calculated by the method proposed by DeLong et al. To create the tumor subvolume defined by combining more than one cPC, the maximum AUC were used to determine the $\{\beta_i\}$.

Figure 3:
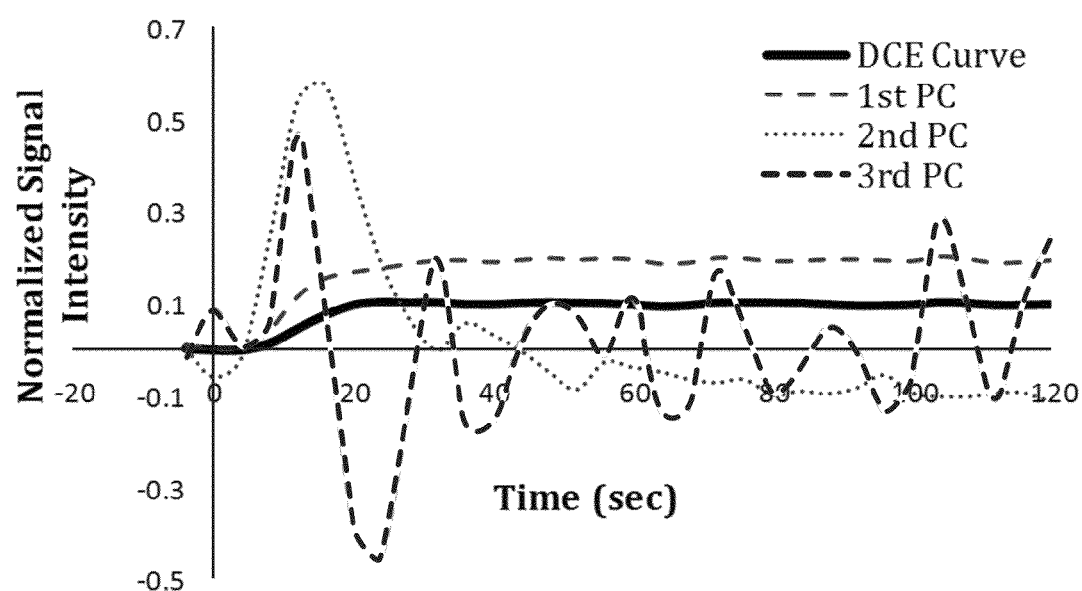
FIG. 3 is a depiction of a graph that illustrates examples of a typical DCE curve of a voxel in a brain metastatic lesion and the first three principal components.

Results; Principal Components: PCA revealed that the first three principal components (PCs) comprised more than 99.99% of the energy of the DCE curves of brain metastases, of which the first component contributed approximately 99.8% while the second and third components had 0.08% and 0.02% contributions, respectively, as shown in FIG. 3. Further investigation revealed that the first component is related to the area under each DCE curve, while the second and third ones were associated with the enhancement rate of a DCE curve and its derivative, respectively. Therefore, the analysis described in the method section was applied to the histograms of the first three cPCs in a tumor to determine the subvolume of the tumor with a given class.

TABLE 5

Differences between responsive, stable and progressive brain metastases using cPC defined tumor subvolume, physiological defined tumor subvolume and conventional metrics

| | | Group of lesions | | | |
|---|---|---|---|---|---|
| | | Analysis | Post Analysis | | |
| | Metric | R vs. {S & P} | R vs. S | S vs. P p-value | R vs. P |
|---|---|---|---|---|---|
| Projection Coefficient Defined Tumor Subvolumes | $\hat{\text{ASV}}_{Pre \to 2W,j}(a_1)$ j = low | 0.5937 | 0.8766 | 0.7024 | 0.3878 |
| | j = intermediate | 0.0773 | 0.2477 | 0.3339 | 0.0457 |
| | j = high | 0.0017\*\* | 0.0199\* | 0.1321 | 0.0015\*\* |
| | $\hat{\text{ASV}}_{Pre \to 2W,j}(a_2)$ j = low | 0.4843 | 0.7431 | 0.7702 | 0.3359 |
| | j = intermediate | 0.5774 | 0.8766 | 0.2002 | 0.1596 |
| | j = high | 0.0661 | 0.3979 | 0.0561 | 0.0096\*\* |
| | $\hat{\text{ASV}}_{Pre \to 2W,j}(a_3)$ j = low | 0.0094\*\* | 0.0068\*\* | 0.2002 | 0.1323 |
| | j = intermediate | 0.4133 | 0.7693 | 0.2909 | 0.2083 |
| | j = high | 0.8403 | 0.1522 | 0.0143 | 0.1088 |
| | $\hat{\text{ASV}}_{Pre \to 2W,high,low}(a_1, a_3, 0.3)^{\wedge}$ | 0.0005 | 0.0018 | 0.3568 | 0.0053 |
| Physiological Defined Tumor Subvolumes | $\hat{\text{ASV}}_{Pre \to 2w,high}$(rCBV) | 0.0057\*\* | 0.0338\* | 0.3568 | 0.0072\*\* |
| | $\hat{\text{ASV}}_{Pre \to 2W,high}(k^{trans})$ | 0.4992 | 0.6663 | 0.0162\* | 0.0406\* |
| | $\hat{\text{ASV}}_{Pre \to 2W,high,high}$(rCBV, $k^{trans}$, 0.6) | 0.0015\*\* | 0.0199\* | 0.0687 | 0.0012\*\* |
| Conventional Metrics | $\hat{\Delta}\mu_{Pre \to 2W}$(rCBV) | 0.0066\*\* | 0.0049\*\* | 0.2336 | 0.1088 |
| | $\hat{\Delta}\mu_{Pre \to 2W}(k^{trans})$ | 0.8775 | 0.5233 | 0.1704 | 0.5704 |
| | $\hat{\Delta}\text{GTV}_{Pre \to 2W}$ | 0.0124\* | 0.1086 | 0.0653 | 0.0039\*\* |

Abbreviations:
GTV = gross tumor volume;
R = responders;
S = stables;
P = Progressive;
cPC = projection Coefficient;
$^{\wedge}$The optimum value of $\beta_3$ is 0.3, see the results of the ROC analysis.
\*P < 0.05;
\*\*P < 0.01.
The candidate subvolume for each principle component is highlighted.

Association of the cPC-Defined Tumor Subvolumes with Response: associations of the changes in the first three cPC-defined brain metastases subvolumes with high, intermediate or low coefficients from pre-RT to 2 W with the tumor response to treatment are given in Table 5. Since the first three components were only compared, a p-value<0.01 was considered as significance to select the candidate parameters. It was found that for the responsive group, a percentage decrease in the high-a1 subvolumes of the tumors from Pre-RT to 2 W differed significantly from the group combining progressive and stable tumors (p<0.0017), Table 5. It was observed a similar but weaker trend for the high-a2 subvolume (p<0.07). Furthermore, a percentage decrease in the low-a3 subvolume of the tumor was associated with tumor response (p<0.01). A percentage decrease in the subvolumes defined by combining the high-a1 and low-a3 classes from pre-RT to 2 W revealed that adding a3 improved the statistical significance for differentiating the responsive tumor from the group of stable and progressive lesions compared to either coefficient alone but a2 did not add discriminatory information. As a post analysis, the comparisons between other lesion groups are also given in Table 5.

Figure 4C:
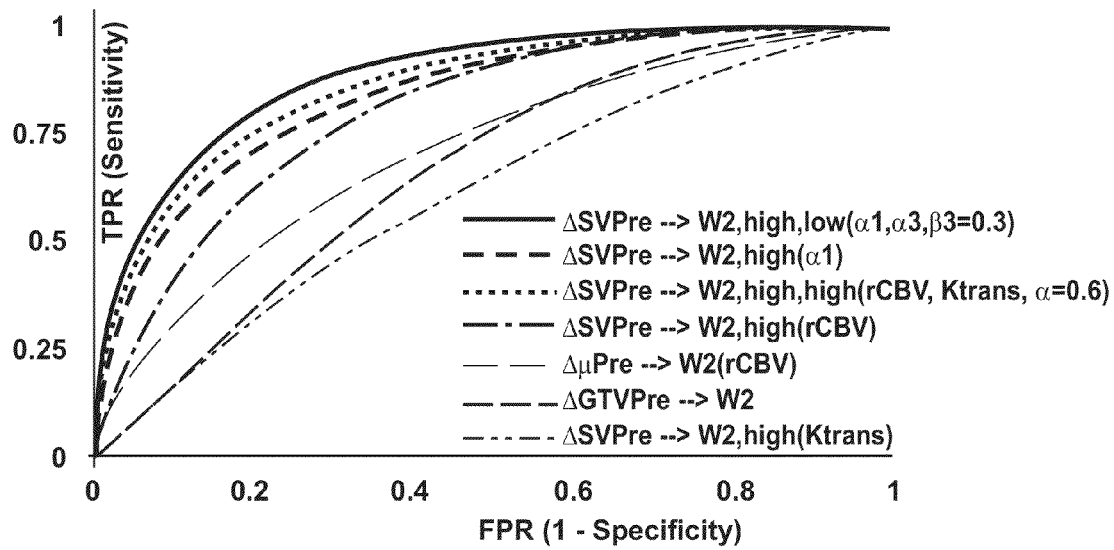
FIG. 4C is a depiction of a graph that illustrates Receiver Operating Characteristic curves of the metrics in Table 5 for predicting responsive tumors.
Figure 4D:
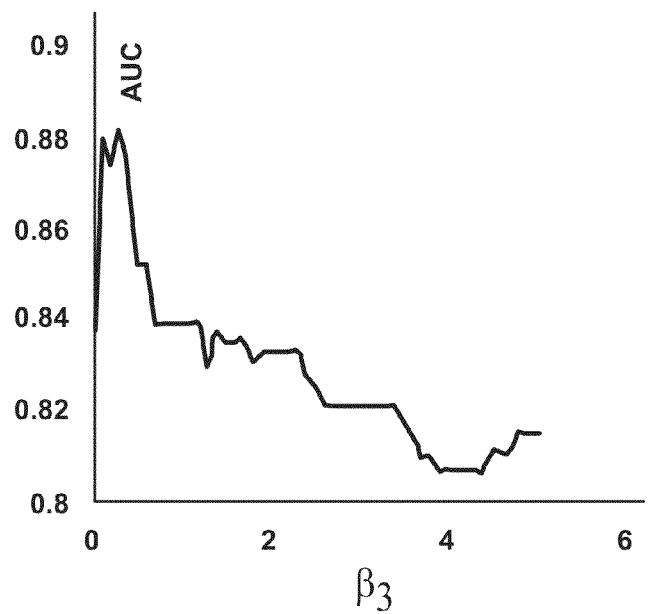
FIG. 4D is a depiction of a graph that illustrates area under the ROC curves vs. $\alpha$ in Equation (20)

Predictive Values of the cPC-Defined Tumor Subvolumes: it was explored that the predictive value of the decrease in the subvolumes of the brain metastases defined by the cPCs from Pre-RT to 2 W for predicting responsive tumors post-RT, and compared their performance with the decrease in subvolumes of the tumors defined by the high rCBV and high Ktrans and two conventional metrics. The ROC analysis showed that the AUCs were 0.83±0.06 (±SEM), 0.77±0.07, 0.80±0.07, 0.70±0.08, 0.67±0.08 and 0.56±0.09 for $\hat{A}SV_{Pre \to 2W, high}$ ($\alpha_1$), $\hat{A}SV_{Pre \to 2W, low}$ ($\alpha_3$), $\hat{A}SV_{Pre \to 2W, high}$ (rCBV), $\hat{\Delta}\mu_{Pre \to 2W}$(rCBV), $\hat{\Delta}GTV_{Pre \to 2W}$ and $\hat{A}SV_{Pre \to 2W, high}$ ($K^{trans}$), respectively, as shown in FIGS. 4C and 4D, indicating the high-a1 defined subvolume of the tumor had the best performance among the tested variables for predicting responsive tumor. The subvolumes defined by the high-a1 and low-a3 classes with the weighting factor=0.3, determined by empirical evaluation of the AUCs as shown in FIG. 4D, resulted in the largest AUC, 0.88±00.5. The subvolumes defined by the high-rCBV and high-Ktrans classes with the weighting factor=0.6 resulted in the AUC of 0.86±0.06.

C. Apparent Diffusion Coefficients in Subvolume Analysis

While the techniques discussed above (i.e., the PK modeling techniques and the PCA techniques) measure the vascular properties of the tumor, other techniques that measure cellularity may be used in conjunction with the subvolume analysis of FIG. 10. Cellularity may be determined by obtaining imaging-derived cellularity feature data that measures the water mobility in the tissue of the tumor via a diffusion weighted magnetic resonance (DW-MRI). Similar to vascularity subvolume analysis inputs (i.e., the PK modeling technique and PCA technique), as discussed above, the cellularity features of subvolumes of tumors may be utilized to predict treatment outcome as well as shown in FIG. 10.

II. Diffusion Abnormality Index Analysis

The DAI technique herein is similar to the subvolume analysis technique, as discussed above, in that it uses the imaging-derived data to predict tumor response to therapy. However, this DAI technique develops a DAI to quantify the extent of abnormality of the tumor ADC histogram compared to normal tissue. A normal tissue ADC histogram, HNT (ADC), may be obtained in a normal brain volume of 3-4 cc with the peak normalized to 1. The tumor ADC histogram that usually spreads beyond HNT (ADC) is divided by HNT (ADC) into 3 categories: low (high cellularity), normal, and high (edema and necrosis) ADC. An abnormal diffusion probability function (DAProF) of the tumor may be then defined by 1-HNT (ADC) and band-pass filtered to reduce noise influence at the two tails of the histogram. Given that changes in low and high ADCs could have different roles in response assessment, a factor ($0<\alpha<1$) may be used to weight the low ADC contribution to the DAProF related to high ADC's. As a result, an integral of the DAProF-weighted tumor ADC histogram may be calculated and used to define the DAI.

In an example, the DAI changes were evaluated to differentiate responsive, stable and progressive lesions in 24 patients who had brain metastases and were treated by either whole brain radiation therapy (WBRT, 28 mostly radiosensitive lesions) alone or combined with Bortezomib as a radiation sensitizer (39 radioresistant lesions). The performance of DAI for predicting the post-treatment radiographic response was also evaluated by Receiver Operating Characteristic analysis and compared with changes in gross tumor volume (GTV) observed during the same time interval. In lesions treated by WBRT alone, the responsive tumors showed a greater decrease in DAI at week 2 after starting the radiation than stable and progressive lesions (p<0.00004). The performance of DAI worsened for the radioresistant lesions treated by WBRT combined with Bortezomib but still better than changes in the GTV, suggesting that the physiological change occurs prior to the volumetric change.

To determine cellularity, the DW-MRI is used and has been shown to be an imaging biomarker for assessing tumor aggressiveness and early response to therapy in various cancers. The DW-MRI acquisition is rapid and noninvasive, and uses neither exogenous contrast agent nor ionizing radiation. The apparent diffusion coefficient, quantified from DW-MRI, measures water mobility in tissue, and is sensitive to cellular density, extracellular space tortuosity, and intactness of cellular membranes. However, quantification of an ADC change in the tumor is still a challenge and affects sensitivity and specificity of diffusion indices for early prediction of tumor response to therapy, mainly because the ADCs in a tumor manifest a heterogeneous distribution pattern, due to spatial variation in cellular density, cell structure and water content. In a high cellular region, mobility of water molecules is restricted, and thus the ADC is low; while in a region with necrosis or edema, water molecules move more freely and hence the ADC is high. Animal studies have shown that the ADC in a tumor is inversely correlated with the tumor cellularity. When a tumor responds to treatment, the ADC in the high cellular region could increase due to cell shrinkage followed by phagocytosis or necrosis. Also, the ADC in the edema region could decrease due to drainage of water. Thus, the direction of the change depends on the measurement location of the ADC and the original value of the ADC. Therefore, the heterogeneity in the tumor ADCs and the complex changes that occur after treatment suggest that a change in the mean ADC of a tumor may be a poor indicator for therapy response.

Thus far, several methodologies have been proposed to quantify the ADC changes in tumors, beyond a change in the mean ADC of a tumor, for response assessment. The functional diffusion map (fDM), probably the most common approach, measures the voxel-to-voxel interval changes in a pair of the co-registered ADC images acquired pre and post the start of therapy. The voxels with an ADC change above a threshold are considered as a measure of response. Despite the promising results of the fDM-based approach and its modifications, again, the issue of voxel-to-voxel misregistration, particularly in the region where a tumor volume shrinks or grows during the interval of measurements, is problematic. Also, since the decrease/increase in regions of high cellularity or edema could have different interpretations, it is important to consider the initial ADC values to interpret subsequent changes correctly. Alternatively, analysis of the tumor ADC histogram has been proposed. A bi-normal distribution mixture model has shown that the mean value of the low-ADC distribution can predict therapy response in gliomas. Also, changes in mean, skewness and kurtosis of the ADC histogram or the minimum value of the ADC in tumors have been related to survival and the treatment outcome. However, these methods have not considered changes in the whole ADC histogram, including both regions with high cellularity and edema, in each of which a change could reflect a part of the process of a tumor response to therapy and therefore may lead to losing information from the analyses. Thus, it is highly desirable to develop a new methodology for quantifying the tumor ADCs to improve the performance of DW-MRI for therapy assessment.

Experiment 4

The techniques herein use the DAI to quantify the extent of diffusion abnormality of brain metastases for early prediction of tumor response to therapy. For instance, brain metastases, which are the most prevalent form of intracranial cancer, exceed the number of primary brain tumors by at least ten times and occur in approximately 25% of all cancer patients. In a DAI-based approach, an abnormal diffusion probability was assigned to each voxel of the tumor based upon its ADC value relating to the normal tissue ADC distribution. Then, a DAI of the tumor was obtained by summing all the abnormal probabilities within the lesion. It was tested whether an early change in the DAI could predict response of brain metastases in the patients who were treated by either whole brain radiation therapy alone or in combination with Bortezomib as a radiation sensitizer.

Figure 11A:
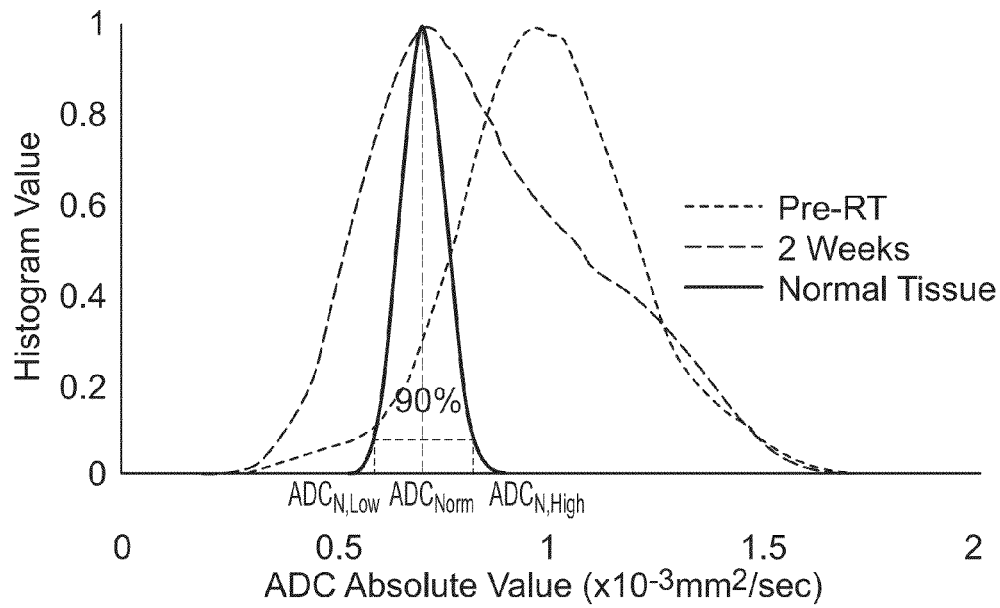
FIG. 11A is a depiction of a graph that illustrates examples of apparent diffusion coefficients histograms in a region of normal white matter, a progressive brain metastasis prior to treatment and two 2 weeks after starting treatment.
Figure 11B:
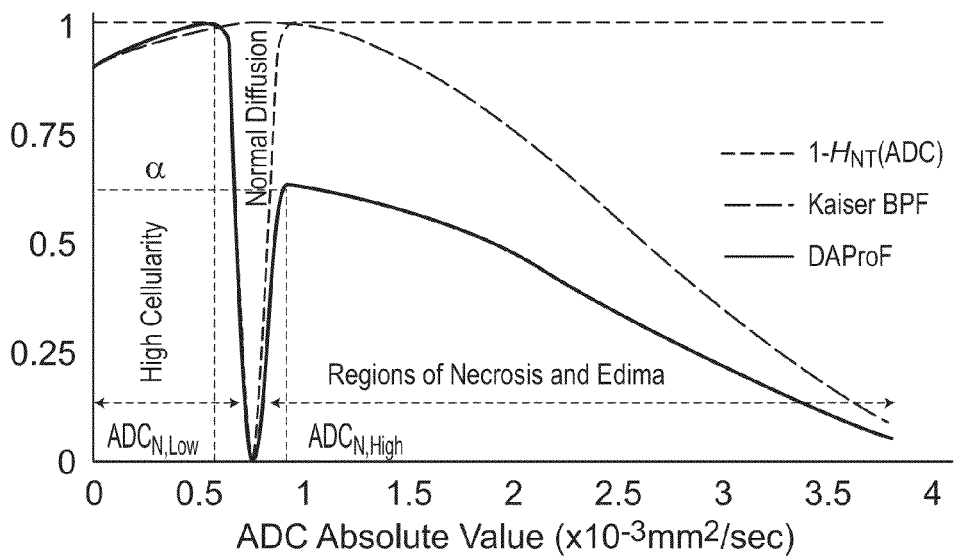
FIG. 11B is a depiction of a graph that illustrates an example Diffusion Abnormality Probability Function of the same tumor as shown in FIG. 11A.

Histogram of ADCs in a Tumor: to analyze the ADC distribution in a tumor and a subsequent change during treatment, a histogram of ADCs in a lesion measured at each time point was generated with 150 evenly-spaced bins that cover the ADCs of all lesions of interest. The ADC histogram, H(ADC=x), of a lesion is calculated as:

$$H(ADC=x) \equiv n_i: x-\epsilon \leq ADC_i \leq x+\epsilon \quad (21)$$

where $n_i$ is the number of voxels within $|ADC_i - x| < \epsilon$, and $$\varepsilon = \frac{\sigma}{4},$$

a smooth factor of H, where $\sigma$ is a standard deviation of the ADC distribution in the tumor. Then, the ADC histogram of each lesion at each scan is normalized to have an area under the histogram equal to one ($\int H(x)=1$). The ADC histogram of normal tissue ($H_{NT}(ADC)$) is calculated in a similar fashion except the peak is normalized to one. FIG. 11A depicts examples of (i) ADC histograms in a region of normal white matter (solid line), and (ii) a progressive brain metastasis prior to treatment (dotted line) and 2 weeks after starting the treatment (dashed line). As shown in FIG. 11A, the ADC histogram of a tumor spreads widely, and is skewed and/or shifted when compared to the normally distributed ADC histogram of normal tissue. On the other hand, FIG. 11B depicts the DAProF of the same tumor (solid lines) in which the DAProF is equal to $(1-H_{NT}(ADC))$ filtered by Kaiser band-pass filter and weighted by a factor $\alpha$ (<1) for high ADCs.

Diffusion Abnormality Probability Function:

next, a diffusion abnormality probability function (DAProF) was developed to characterize the whole tumor ADC histogram based upon the normal tissue ADC distribution of each patient. The HNT(ADC) divides the tumor ADC histogram into three segments with low, normal, and high ADCs (FIG. 11B). The first and latter are related to high cellular density and edema, respectively. Therefore, for each patient, a DAProF can be defined as $1-HNT(ADC)$, and filtered by Kaiser band-pass filter (BPF) centered at the peak of HNT(ADC) to reduce noise influence in the computation at two tails where the ADC approaches to positive or negative infinite (or zero) as:

$$DAProF = BPF \cdot (1 - H_{NT}(ADC)) \quad (22)$$

Eq. (22) denotes the tumor ADCs are abnormal except in the areas where the ADC values are in the range of normal tissue ones. In Eq. (22), 90% of confidence interval of HNT (ADC) is used to define the band-width of BPF. Because that changes in the low-ADC (high cellularity) tumor region could be associated with therapy response differently, a weighting factor $\alpha$ (<1) is used to weight low and high ADC contributions unequally in the DAProF$\alpha$ as:

$$DAProF_\alpha = \quad (23)$$
$$\begin{cases} DAProF_{Low} = BPF \cdot (1 - H_{NT}(ADC)) & ADC \leq ADC_{Norm} \\ DAProF_{High} = \alpha \cdot BPF \cdot (1 - H_{NT}(ADC)) & ADC > ADC_{Norm} \end{cases}$$

where $ADC_{norm}$ is the ADC at the peak of the normal tissue-histogram. Finally, the DAProF$_\alpha$ is normalized to one at the peak. Note that DAProF$_\alpha$ is patient-specific.

Diffusion Abnormality Index:

to quantify the extent of diffusion abnormality in a tumor at a specific scan time ($\tau$), DAI is defined as:

$$DAI_\alpha(\tau) = GTV_\tau \cdot \int H_\tau(x) \cdot DAProF_\alpha(x) dx \quad (24)$$

where GTV and H (x) denote the gross tumor volume and the normalized tumor ADC histogram at time $\tau$, respectively. As a result, the DAI is a summation of diffusion abnormality from all voxels of a tumor. It is worthwhile to note that the DAI is minimum for normal tissue. A low or high ADC abnormality index can also be obtained by replacing DAProF by DAProF$_{Low}$ or DAProF$_{High}$ in Eq. (24). Finally, a change in the DAI from pre-RT to 2 W is calculated as:

$$\Delta DAI_{\alpha pre \to 2W} = \frac{DAI_\alpha(2W) - DAI_\alpha(pre-RT)}{DAI_\alpha(pre-RT)} \cdot 100. \quad (25)$$

In response to therapy, the ADCs in the region with high cellularity may increase due to cell shrinkage or necrosis, and in the region of edema may decrease due drainage of water into tumor cells. However, Eq. (25) combines the two contributions into a single metric for assessing tumor response to a specific therapy regimen.

Patient Sample:

twenty four patients who had brain metastases and were treated by WBRT were enrolled in an institutional review board (IRB)-approved prospective MRI study (12 women and 12 men, ages 40-76 years, Table 6). The histology included melanoma (14), non-small cell lung cancer (6), renal cell carcinoma (1), breast cancer (2), and head & neck squamous cell carcinoma (1). All patients received WBRT with a total dose of 30 Gy (16 patients) or 37.5 Gy (8 patients). Thirteen patients, with radioresistant metastases, also received Bortezomib during WBRT as a radiation sensitizer. Each lesion was analyzed individually due to intra-patient heterogeneous lesion response to therapy. If a patient had three metastases or fewer, all lesions were included. If a patient had more than three lesions, only the three largest lesions were analyzed. If a patient had more than three lesions larger than 0.5 cm3, all lesions larger than 0.5 cm3 were included. As a result, a total of 67 metastatic lesions were included in the dataset, of which 28 were treated with radiation therapy alone and the remaining lesions were treated with radiation therapy in combination with Bortezomib as a radiation sensitizer.

TABLE 6

Patient characteristics information
Patient characteristics information

| Pt. | Gender | Age(Y) | Histology | Total accumulated dose/Fx (Gy) | Concurrent Therapy | No. of L. | Tumor Volume Range (cm$^3$) |
|---|---|---|---|---|---|---|---|
| 1 | Female | 54 | Breast Cancer | 37.5/2.5 | None | 6 | 0.5-11.78 |
| 2 | Female | 60 | NSC Lung Cancer | 37.5/2.5 | None | 1 | 0.52 |
| 3 | Male | 52 | NSC Lung Cancer | 30/3 | None | 1 | 0.479 |
| 4 | Female | 64 | NSC Lung Cancer | 37.5/2.5 | None | 1 | 0.11 |
| 5 | Male | 43 | Head & Neck SCC | 30/3 | None | 1 | 0.60 |
| 6 | Male | 58 | NSC Lung Cancer | 30/3 | None | 3 | 2.38-10.69 |
| 7 | Female | 66 | NSC Lung Cancer | 37.5/2.5 | None | 1 | 0.95 |
| 8 | Female | 53 | Breast Cancer | 30/3 | None | 4 | 0.45-8.9 |
| 9 | Male | 40 | Melanoma | 37.5/2.5 | None | 3 | 0.06-1.23 |
| 10 | Male | 58 | Melanoma | 30/3 | None | 4 | 0.48-6.47 |
| 11 | Female | 51 | NSC Lung Cancer | 30/3 | None | 3 | 0.50-4.55 |
| 12 | Male | 63 | Renal Cell Carcinoma | 30/3 | Bortezomib | 2 | 13.23-14.67 |
| 13 | Male | 41 | Melanoma | 37.5/2.5 | Bortezomib | 3 | 0.15-1.24 |
| 14 | Female | 52 | Melanoma | 37.5/2.5 | Bortezomib | 1 | 2.74 |
| 15 | Female | 45 | Melanoma | 30/3 | Bortezomib | 1 | 2.07 |
| 16 | Male | 49 | Melanoma | 30/3 | Bortezomib | 2 | 0.17-4.09 |
| 17 | Male | 61 | Melanoma | 37.5/2.5 | Bortezomib | 7 | 0.5-17.67 |
| 18 | Female | 55 | Melanoma | 30/3 | Bortezomib | 2 | 0.42-0.55 |
| 19 | Male | 76 | Melanoma | 30/3 | Bortezomib | 1 | 0.68 |
| 20 | Female | 46 | Melanoma | 30/3 | Bortezomib | 8 | 0.5-1.95 |
| 21 | Female | 57 | Melanoma | 30/3 | Bortezomib | 2 | 0.94-1.58 |
| 22 | Male | 60 | Melanoma | 30/3 | Bortezomib | 3 | 0.18-1.31 |
| 23 | Female | 74 | Melanoma | 30/3 | Bortezomib | 4 | 0.69-5.81 |
| 24 | Male | 67 | Melanoma | 30/3 | Bortezomib | 3 | 0.62-11.10 |

Abbreviation:
Pt. = patient;
Y = year;
NSC = non-small cell;
SCC = squamous cell carcinoma;
No. of L. = number of lesions; and
Fx = fraction size.

Image Acquisition and Pre-Processing:

all patients had MRI scans on a Philips 3T scanner prior to radiation therapy (Pre-RT), 2 weeks after the start of RT (2 W), and 1 month after the completion of treatment (1 M Post-RT). MRI scans included pre and post Gd-DTPA volumetric T1-weighted images, 2D T2-weighted images, and diffusion-sensitive images. The diffusion weighted images were acquired using a spin-echo echo-planar imaging sequence (TR/TE=2636/46 msec) with b0=0, and diffusion weighting along three orthogonal directions and b1=1,000 sec/mm2 to calculate the ADC images.

Using an in-house software package, all ADC images were co-registered to pre-RT post-Gd T1-weighted images by rigid transformation and mutual information to have a voxel size of 0.94×0.94×3 (mm3). After each lesion of interest was contoured on the post-Gd T1 weighed images obtained pre-RT, 2 W and 1 M post-RT by a physician, the tumor volumes were transferred onto the ADC maps obtained at the same time point. For each patient, a volume of 3-4 cc of normal white matter or cerebellum tissue, depending upon the location of the tumor of interest, was contoured on the pre-RT post-Gd T1-weighed images and transferred onto the pre-RT ADC map to obtain a distribution of normal ADCs.

DAI for Prediction of Response:

given that previous studies indicate that brain metastases exhibit little pseudo-response and pseudo-progression one month after RT, a percentage change in the gross tumor volume (GTV) from Pre-RT to 1 month post RT, $\hat{A}GTV_{Pre \to 1M post}$, was used as a measure of tumor response to therapy. Data was used to verify that there was little pseudo-response or pseudo-progression in brain metastases treated by either WBRT alone or WBRT with Bortezomib. From Pre-RT to 1 M Post-RT, of the 27 lesions treated with radiation therapy alone, 14 had a decrease in the GTV of at least 25%, defined as responsive, 7 had an increase of at least 25%, defined as progressive, and the remaining 6 were defined as stable. For the 39 lesions treated by radiation therapy in combination with Bortezomib, 10 lesions were responsive, 13 lesions were progressive and 17 lesions were stable.

Predictive Model:

$\alpha(<1)$ in $\hat{A}DAi_{\alpha,pre-RT \to 2W}$ was optimized in each treatment group by maximizing the group difference between the responsive and progressive lesions using Mann-Whitney U Test. Using the optimal value of $\alpha$, it was further tested if $\hat{A}DAi_{\alpha,pre \to 2W}$ could differentiate responsive from stable tumors, and stable from progressive tumors in both treatment groups. A p-value<0.05 was considered as significant. Next, sensitivity and specificity of $\hat{A}DAi_{\alpha,pre \to 2W}$ for predicting non-responsive tumors was tested, including both progressive and stable tumors by Receiver Operating Characteristic (ROC) analysis (software package ROCKIT). Also, the performance of $\hat{A}DAI$ for predicting post-treatment response was compared with the ADC metrics previously published by others, such as a mean of the low ADC distribution from the bi-normal ADC distribution mixture model, and skewness and kurtosis of tumor ADC histograms, and conventional metrics, such as a percentage change in the GTV, pre-treatment minimum ADC, a minimum ADC change and a change in the mean of tumor ADCs from pre-RT to 2 W. The significant difference of the area under ROC curves (AUC) between the metrics were compared by t-test, for which the standard errors and the difference between the two AUCs were calculated by the method proposed by DeLong et al. The leave-one-out technique was used to measure the prediction risk of $\hat{\Delta}$DAI. Considering that melanoma metastasis is more radiation therapy resistant than the metastases from NSC Lung and breast cancers, the two patients with melanoma metastases from the analysis of the first treatment group were excluded to verify whether including melanoma metastases in this group alters the results.

Association of DAI with Response:

the best separation of the group difference between the responsive and progressive tumors resulted in α values of 0.7 and 0.2 for lesions treated with radiation therapy alone and in combination with Bortezomib as a radiation sensitizer, respectively, suggesting that decreases in abnormality associated with high-ADCs (edema/necrosis) may have different roles in response assessment, depending on the treatment regimen and tumor type.

For lesions treated with radiation therapy alone, as anticipated, the DAI showed a significantly greater decrease from Pre-RT to 2 W in the responsive tumors than the progressive ones ($p<0.0003$), but also the stable lesions ($p<0.0035$) or the non-responsive tumors (including both progressive and stable ones) ($p<0.00004$) revealed a decrease as well, as shown in Table 7. For the volumetric change observed during the same period, the percentage decrease in the GTV in the responsive group differed significantly from the stable group ($p<0.03$), the progressive group ($p<0.0004$), and the group of combining the progressive and stable tumors ($p<0.0003$). For the metrics that are often found in literature, their performances for differentiation of responsive, stable and progressive lesions are summarized in Table 7. As seen, skewness was able to differentiate between the responsive and progressive lesions, but worse than the percentage changes in the GTV and DAI for the radiation therapy-alone group. The mean of the low ADC distribution determined from the bi-normal Gaussian mixture model could not differentiate the responsive tumors from progressive or stable ones.

For the radiation resistant lesions treated with radiation therapy combined with Bortezomib, the DAI change from Pre-RT to 2 W was able to differentiate between the responsive and progressive lesions ($p<0.01$), but not between the responsive and stable lesions (see Table 8). Other commonly used metrics could not differentiate any groups. Finally, FIG. 2. shows the box plots of the significant metrics (ΔDAI, ΔGTV, ΔSkewness, and ΔKurtosis) listed in Tables 7 and 8 for responsive, stable and progressive lesions treated with radiation therapy alone or in combination with Bortezomib.

TABLE 7

Association of the different diffusion metrics with response in lesions treated by whole brain radiation therapy alone.

| Metric (Pre-RT->Week2) | Lesion Response Groups | | | |
| --- | --- | --- | --- | --- |
| | R vs. S | S vs. P | R vs. P | R vs. {S & P} |
| | | p-value | | |
| $\Delta DAI_{0.7}$ | 0.003 | 0.004 | 0.0003 | 0.00004 |
| ΔGTV | 0.02 | 0.004 | 0.0004 | 0.0003 |
| ΔSkewness | 0.29 | 0.44 | 0.02 | 0.03 |
| ΔKurtosis | 0.41 | 0.73 | 0.06 | 0.08 |
| Δμ | 0.29 | 0.62 | 0.57 | 0.31 |
| ΔMinADC | 0.33 | 0.13 | 0.29 | 0.92 |
| $MinADC_{preRT}$ | 0.55 | 0.23 | 0.77 | 0.89 |

TABLE 7-continued

Association of the different diffusion metrics with response in lesions treated by whole brain radiation therapy alone.

| Metric (Pre-RT->Week2) | Lesion Response Groups | | | |
| --- | --- | --- | --- | --- |
| | R vs. S | S vs. P | R vs. P | R vs. {S & P} |
| | | p-value | | |
| ΔLow-ADC (BNGM) | 0.03 | 0.23 | 0.62 | 0.31 |
| $Low\text{-}ADC_{preRT}$ (BNGM) | 0.09 | 0.03 | 0.35 | 0.71 |

Δ = Change from Pre-RT to Week 2;
μ = mean of tumor ADC;
Min = minimum;
Low-ADC (BNGM) = the mean of the low ADC distribution in the bi-normal Gaussian mixture model;
GTV = gross tumor volume;
DAI = diffusion abnormality index;
R = responsive;
S = stable;
P = progressive.

Table 7 illustrates the group differences between responsive, stable, and progressive tumors treated with radiation therapy. For each metric, the absolute or percentage change from pre-RT to week 2 were evaluated and the best performance is reported. The black rows show significant metrics.

TABLE 8

Association of the different diffusion metrics with response in radioresistant lesions treated by whole brain radiation therapy in combination with Bortezomib as a radiation sensitizer.

| Metric (Pre-RT->Week2) | Lesion Response Groups | | | |
| --- | --- | --- | --- | --- |
| | R vs. S | S vs. P | R vs. P | R vs. {S & P} |
| | | p-value | | |
| $\Delta DAI_{0.2}$ | 0.25 | 0.03 | 0.01 | 0.04 |
| ΔGTV | 0.93 | 0.07 | 0.16 | 0.50 |
| ΔSkewness | 0.47 | 0.98 | 0.43 | 0.39 |
| ΔKurtosis | 0.89 | 0.77 | 0.73 | 0.78 |
| Δμ | 0.47 | 0.87 | 0.87 | 0.59 |
| ΔMin | 0.13 | 0.52 | 0.27 | 0.13 |
| $Min_{preRT}$ | 0.58 | 0.67 | 0.68 | 0.57 |
| ΔLow-ADC (BNGM) | 0.65 | 0.67 | 0.78 | 0.66 |
| $Low\text{-}ADC_{preRT}$ (BNGM) | 0.58 | 0.94 | 0.82 | 0.68 |

Δ = Change from Pre-RT to Week 2;
μ = mean of tumor ADC;
Min = minimum;
Low-ADC (BNGM) = the mean of the low ADC distribution in the bi-normal Gaussian mixture model;
GTV = gross tumor volume;
DAI = diffusion abnormality index;
R = responsive;
S = stable;
P = progressive.

Table 8 illustrates the group differences between responsive, stable and progressive tumors treated with radiation therapy. For each metric, the absolute or percentage change from pre-RT to week 2 were evaluated and the best performance is reported. The black rows show significant metrics.

Figure 12:
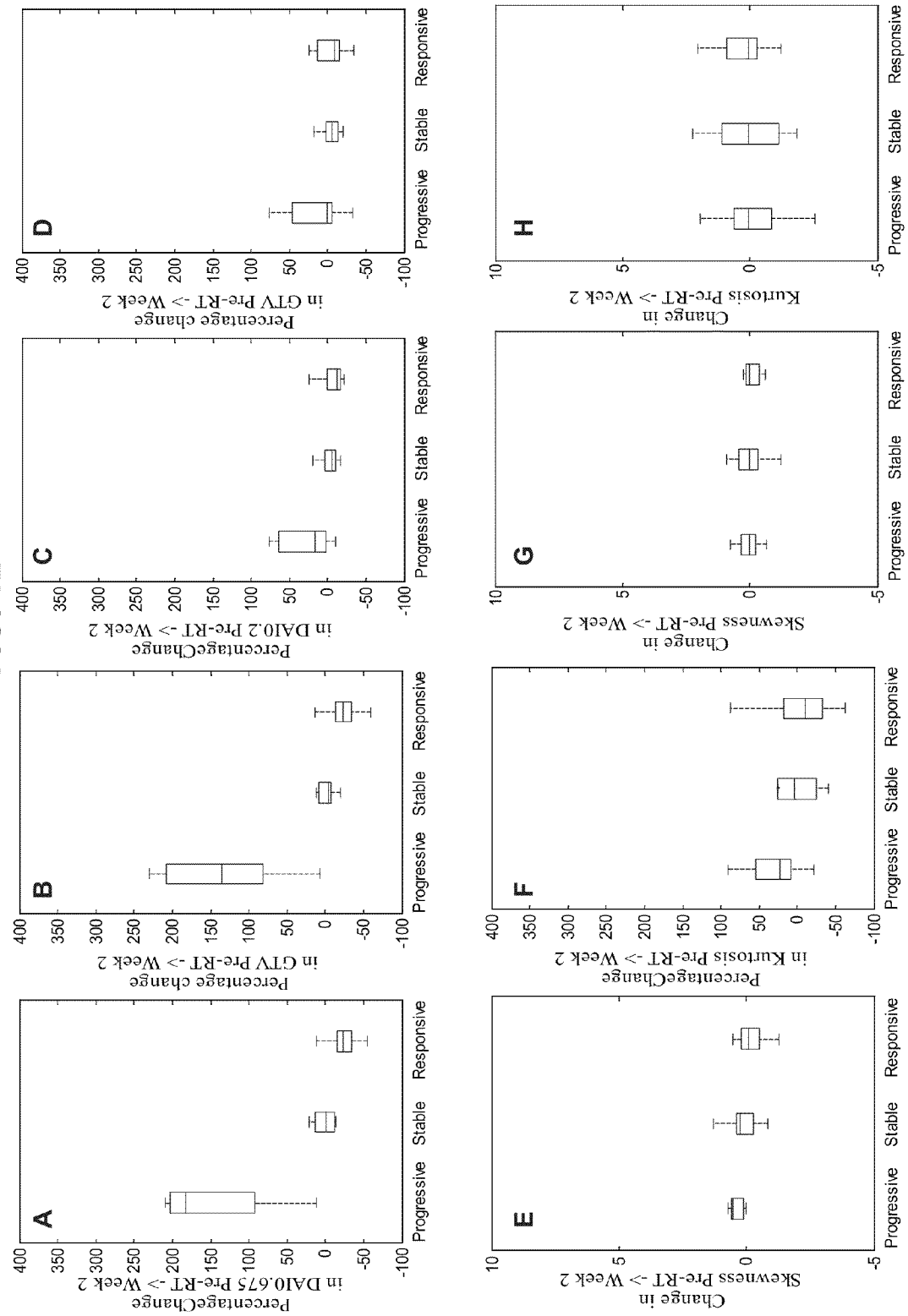
FIG. 12 are exemplary box plots that illustrate the change in different characteristics for responsive, stable, and progressive lesions treated by whole brain radiation therapy or in combination with Bortezomib as a radiation sensitizer.

FIG. 12 depicts box plots of ΔDAI (A and E), ΔGTV (B and F), ΔSkewness (C and G) and ΔKurtosis (D and H) for responsive, stable and progressive lesions treated by WBRT alone (top) or in combination with Bortezomib as a radiation sensitizer (bottom). The top row of FIG. 12 shows that ΔGTV and ΔDAI0.7 differentiate the responsive lesions from the stable and progressive ones treated by WBRT while ΔDAI0.2 differentiate the responsive and stable lesions from the progressive ones when Bortezomib is used as a radiation sensitizer.

Figure 13A:
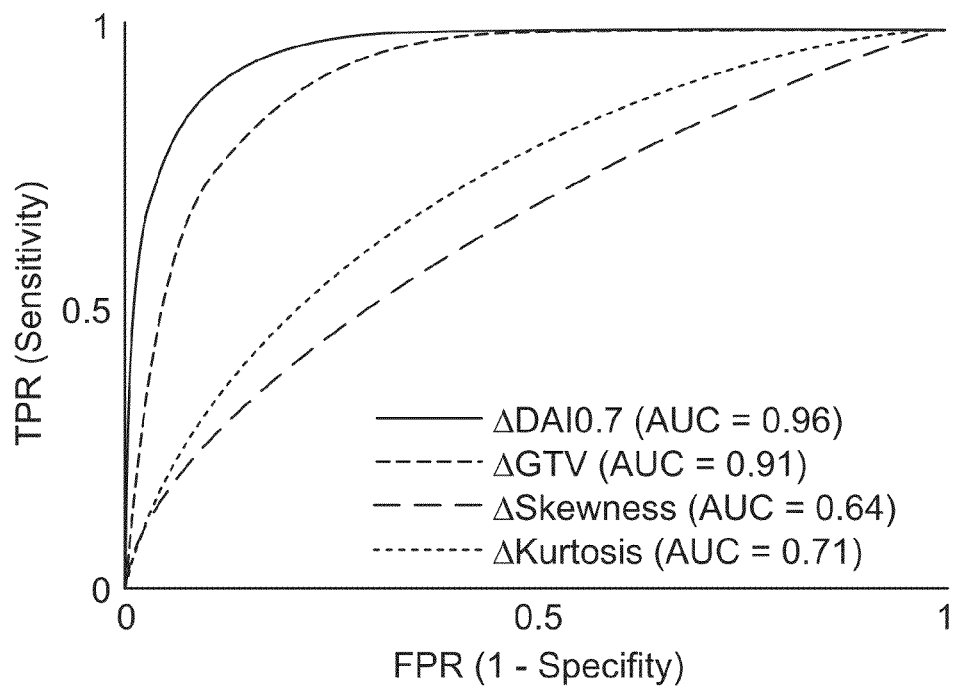
FIG. 13A is a depiction of a graph that illustrates different examples of Receiver Operating Characteristic curves for different characteristics for predicting non-responsive tumors treated with radiation therapy alone.
Figure 13B:
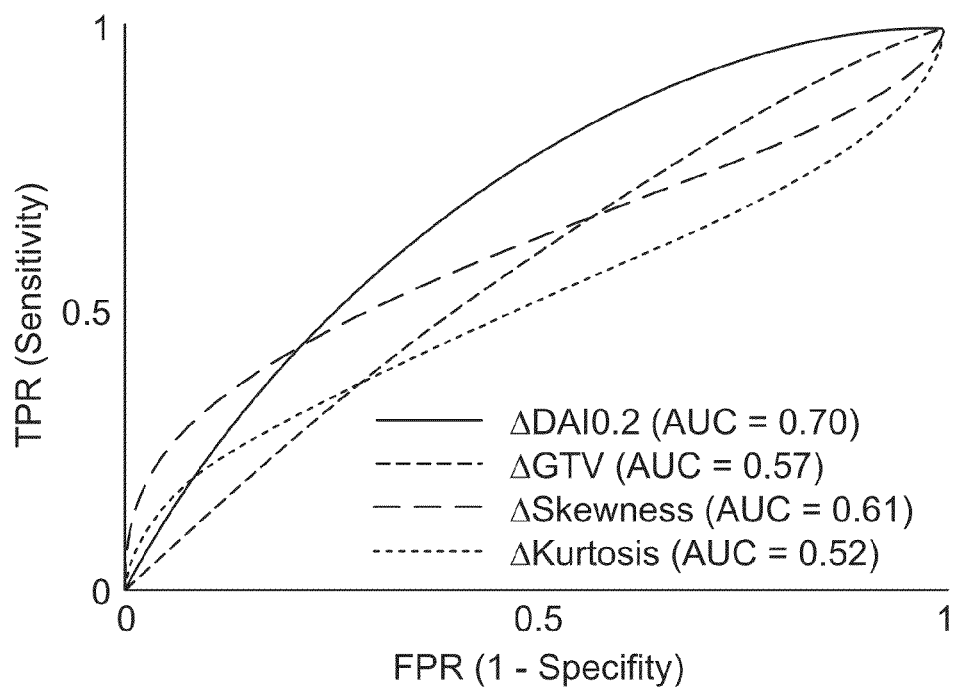
FIG. 13B is a depiction of a graph that illustrates different examples of Receiver Operating Characteristic curves for different characteristics for predicting non-responsive tumors treated with radiation therapy in combination with Bortezomib as a radiation sensitizer.

Performance of the DAI for Prediction of Response:

the performance of the significant or marginally significant metrics in Tables 7 and 8 was evaluated, such as ΔDAI, ΔGTV, ΔSkewness, and ΔKurtosis, for prediction of non-responsive tumors post-RT for both treatments. When lesions treated with radiation therapy alone, the ROC analysis showed that the AUC was 0.96±0.04 (±SEM), 0.91±0.06, 0.64±0.1, and 0.71±0.1 for $\Delta DAI_{0.7}$, ΔGTV, ΔSkewness, and ΔKurtosis, respectively, as shown in FIG. 13A. A pair-wise comparison of the ROC curves of the two metrics revealed that ΔDAI0.7 is a better predictor, but not significantly, than ΔGTV (p<0.15). For 92% sensitivity, ΔDAI0.7 and ΔGTV achieved 87% and 73% specificity, respectively. When Bortezomib was used as a radiation sensitizer, the AUCs of 0.70±0.09 (±SEM), 0.57±0.1, 0.61±0.1, and 0.52±0.1 were achieved for $\Delta DAI_{0.2}$, ΔGTV, ΔSkewness, and ΔKurtosis, respectively, as shown in FIG. 13B. In addition, the leave-one-out analysis resulted in α=0.7±0.0 (SEM) for the lesions treated by radiation therapy alone, and α=0.19±0.02 for the tumors treated by combining radiation therapy with Bortezomib, indicating that there is no significant bias in the α value selection and also that α is a treatment-specific and even disease-specific parameter in the DAI. Finally, exclusion of melanoma metastases from the first treatment group resulted in an AUC of 0.92±0.05, indicating including or excluding the radiation resistant lesions from the first treatment group did not alter the results.

Figure 14:
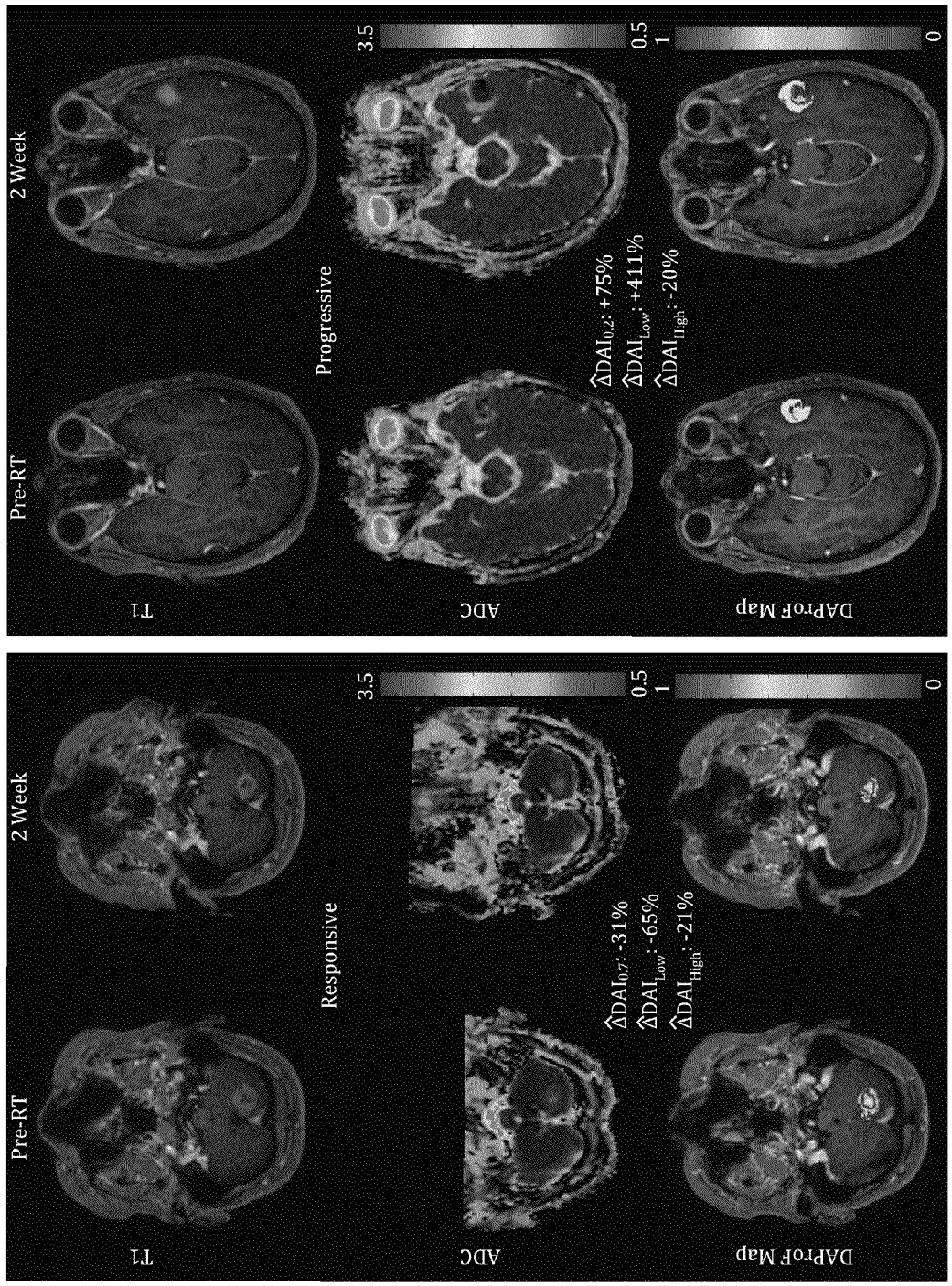
FIG. 14 illustrates exemplary images of T1-weighted images, apparent diffusion coefficient maps, and maps of diffusion abonormality probability functions at Pre-RT and at week 2 for a responsive lesion and for a progressive lesion.

DAProF Map:

examples of maps of the ADC and the diffusion abnormality probability function, DAProF, for a responsive lesion, treated with radiation therapy alone, and a progressive one, treated with radiation therapy in combination with Bortezomib, at Pre-RT and 2 W are shown in FIG. 14. In particular, FIG. 14 depicts T1-weighted images at Pre-RT and 2 W (top rows), ADC maps at Pre-RT and 2 W (middle rows), and maps of diffusion abnormality probability functions at Pre-RT and 2 W (bottom rows) for a responsive and a progressive lesion. The images of a responsive case (with a volume of 3.7 cc) are depicted in two left columns of FIG. 14 and the images of a progressive one (with a volume of 4.1 cc) are represented in two right columns of FIG. 14. From Pre-RT to 2 W, the DAI decreased ~31% for the responsive lesion, and increased ~16% for the progressive one. For the responsive lesion, treated by radiation therapy alone, α=0.7 but for the progressive lesion where Bortezomib was used α=0.2. From Pre-RT to 2 W, the DAI decreased ~31% for the responsive lesion but increased ~75% for the progressive one. For the responsive lesion, the low and high ADC components in the DAIS decreased approximately 65% and 21%, respectively. For the progressive lesion, the low ADC component in the DAI increased 411% but the high ADC one decreased 20%.

FIG. 15 illustrates an example implementation of the DAI techniques herein that depicts a flow diagram illustrating an exemplary method for performing an early assessment of a tumor response to radiation therapy. The method 1500 begins with the system obtaining diffusion weighted-images from a tumor or disease and generating ADCs from the images (block 1502). The system then generates a histogram from the generated ADCs of the tumor (block 1504) and also creates a diffusion abnormality probability function from a ADC histogram of normal tissue (block 1506). The system further creates of diffusion abnormality probability map of the tumor or disease as a visual output or target for focal therapy (block 1508) and generates a DAI from the ADCs of the tumor or disease for diagnosis, prognosis or prediction of treatment (block 1510).

This development of a DAI based upon diffusion weighted magnetic resonance imaging for early assessment of brain metastasis response to radiation therapy uses the physiology of abnormal ADCs in a tumor, including both high cellularity and edema. The DAI weights the abnormal ADC contributions from high cellularity and edema differently for predication of therapy response. The performance of DAI in patients who had brain metastases were evaluated and were treated by either WBRT alone (mostly radiation sensitive lesions) or in combination with Bortezomib as a radiation sensitizer (radiation resistant lesions). Compared to other ADC metric published previously and conventional metrics, the DAI performed better in predicting volumetric response of brain metastases to radiation therapy. Also, the results indicate that the diffusion-related physiological change in the tumor occurs earlier than the morphological change in response to radiation therapy. The DAI may be applied to other tumor types and treatment regimens after recalibration, e.g., glioblastoma and head and neck cancers, and anti-angiogenesis therapy. The DAI may be used as a robust imaging biomarker for early assessment of tumor response and outcome.

In the development of the DAI, the weighting factor, α, was found to be different for different treatments and/or tumor types. For instance, when brain metastases were treated with WBRT alone, the changes in abnormality associating with high-ADCs contributed substantially to response assessment. In this case, both a decrease in cellularity and a decrease in edema could indicate treatment response. However, in the treatment of melanoma metastases to the brain, it was realized that a decrease in abnormality associated with high-ADCs is less important for response assessment. Also, the performance of all tested ADC metrics, including the DAI, was found to be worse for patients with melanoma metastases than for the metastases that were not from melanoma. This could be due to the nature of melanoma, high vascularity, edema and hemorrhage, or, the effect of Bortezomib on the lesion. Because Bortezomib could alter vascular properties of the tumor, a change in vascular characteristics of the tumor may be an important part of tumor response to therapy, and hence a perfusion change could be added into the DAI to improve the response assessment. The findings also suggest that the DAI could be used to assess a specific treatment effect on a specific tumor. For an anti-angiogenesis treatment to brain tumor, e.g., glioblastoma, a high ADC abnormality reduction indicates the treatment effect on the abnormal leaky vasculature but a low ADC abnormality decrease suggest the effect on the tumor.

The DAI may have several advantages in comparison with functional diffusion map, the most common approach in study of the ADC map. The DAI need not rely on voxel-to-voxel image registration accuracy, which the fDM-based analysis solely depends upon. Hence, anatomical alteration of a tumor after starting therapy, e.g., a change in edema, or surgical cavity, and/or tumor growth or shrinkage, does not have an adverse effect on the DAI. In addition, the tumor volume is incorporated into the DAI, and thus a change in DAI represents both physiological and morphological changes in a tumor, which may increase the sensitivity of the DAI for tumor response to therapy. Furthermore, the fDM-based analysis only considers an absolute change in the ADC, regardless of the origin of the ADC, whereas an increase or a decrease in the low or high ADC region has a very different underlying implication. Further, an ADC increase in the region with abnormal low diffusion and a decrease in the region with abnormal high diffusion both are positive indications for a tumor response to therapy. Also, it is important to point out that although a change in the DAI of a tumor does not depend upon voxel-level accuracy of registration of images acquired pre and after the start of therapy, spatial information of diffusion abnormality of a tumor is available at any given measurement, as shown in FIG. 14, which could be used for visualization or provide guidance for intensified treatment.

The DAI may offer several advantages in comparison with other histogram-based approaches. In some of these techniques, only the low-ADC portion of the tumor histogram is used for therapy assessment; yet, a reduction in the abnormal high ADC in the edema region may be also an important indicator for response prediction. Thus, combining the changes in both abnormal low and high ADC regions has the potential to produce a better predictor for assessing response to various treatments. The indices based upon the skewness and kurtosis of the tumor ADC histogram neglect diffusion physiology in a tumor and may not be able to capture the complex change patterns in a heterogeneous tumor for response assessment.

The DAI may be used as a biomarker for assessment of brain metastasis response to WBRT. Currently, WBRT and stereotactic radio-surgery (SRS) are two routine treatments for brain metastases and prolonging patient survival. However, a recent study has shown that WBRT produces a decrease in neurocognitive status compared to SRS. Therefore, more and more patients are receiving focal treatment for brain metastases. As WBRT is being done less, more patients are developing new lesions after treatment of the initial lesions, and thus are being treated to new lesions over time. Also, the DAI could be extended to other tumor types, e.g., glioblastoma, for early assessment of tumor response to therapy.

The techniques disclosed herein may combine the different properties of the subvolumes of a tumor, such as the vascularity of subvolumes of the tumor, the cellularity of subvolumes of the tumor, etc. to calculate a more precise prediction in treatment outcome. For example, the method may utilize vascular properties, such as blood flow, blood volume, etc. in predicting one treatment outcome and also may examine the cellularity properties (i.e., the water mobility in tissue) to determine an abnormal diffusion coefficient in predicting treatment outcome. The prediction results from the both properties may be combined together to provide a more refined, accurate overall prediction for treatment outcome.

Figure 16:
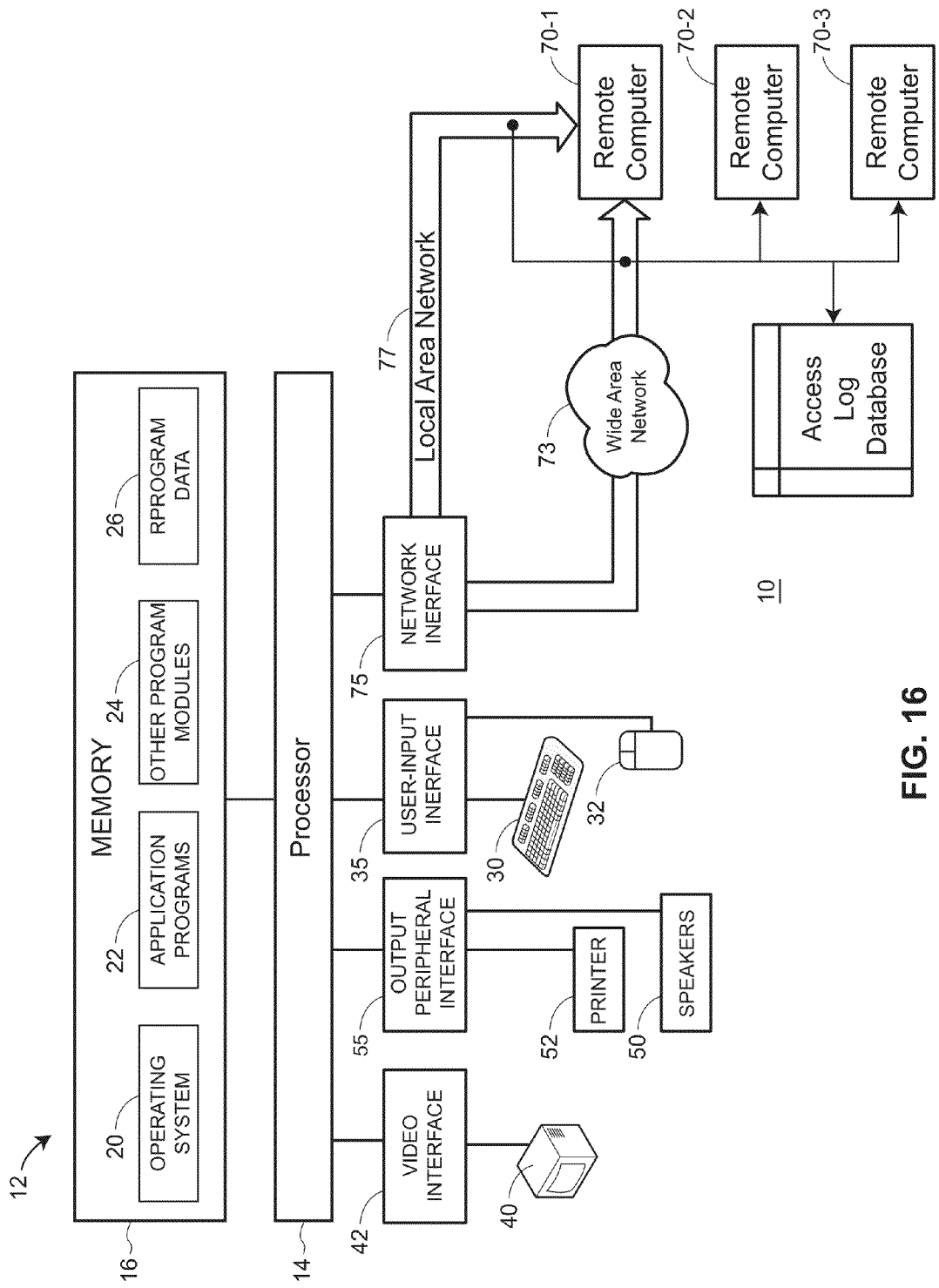
FIG. 16 is a block diagram of an example system in which techniques for predicting of treatment via subvolume identification are implemented.

In the example embodiment illustrated in FIG. 16, a computer system for performing subvolume analysis of a target tissue is provides. The techniques described herein (e.g., in FIGS. 10, 15) may be coded, in software, hardware, firmware, or combination thereof, for execution on a computing device such as that illustrated in FIG. 16. Generally, FIG. 16 illustrates an example of a suitable computing system environment 10 to interface with a medical professional or other user to analyze medical imaging data. It should be noted that the computing system environment 10 is only one example of a suitable computing environment and is not intended to suggest any limitation as to the scope of use or functionality of the method and apparatus of the claims.

With reference to FIG. 16, an exemplary system for implementing the blocks of the claimed methods and apparatuses includes a general-purpose computing device in the form of a computer 12. Components of computer 12 may include, but are not limited to, a processing unit 14 and a system memory 16. The computer 12 may operate in a networked environment using logical connections to one or more remote computers, such as remote computers 70-1, 70-2, . . . 70-n, via a local area network (LAN) 72 and/or a wide area network (WAN) 73 via a modem or other network interface 75. These remote computers 70 may include other computers like computer 12, but in some examples, these remote computers 70 include one or more of a (i) an MRI imaging system, (ii) a CT imaging system, (iii) a PET imaging system, and (iv) a medical records database systems.

Computer 12 typically includes a variety of computer readable media that may be any available media that may be accessed by computer 12 and includes both volatile and nonvolatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Generally, the techniques herein may be coded any computing language for execution on computer 12. Image data may be obtained from the remote computers 70-1, 70-2, . . . 70-n and stored loaded on to any of the computer storage devices of computer 12. Once the image data, including image segments, is obtained, a user may input or select the condition parameters through an input mechanism as described. Although, in other examples, the condition parameters may be pre-selected or automatically determined, for example, based on a particular type of analysis that is to be performed. The output of the executable program may be displayed on a display (e.g., a monitor 40), sent to a printer 52, stored for later use by the computer 12, or offloaded to another system, such as one of the remote computers 70. The output may be in the form of a graph or table indicating the explanation audit. Operations of the system may be recorded in an log database for future reference as shown. This log database may be accessed at subsequent times when a post-RT image is to be obtained, for example. In any event, a subvolume processing engine implementing the processes of FIGS. 10, 15 is implemented on the computer 10, in the illustrated example.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A method of analyzing medical image data of a region of interest in a sample tissue, the method comprising:
    obtaining, at a computer system, the medical image data of the region of interest, the medical image data containing a plurality of image segments;
    identifying, at the computer system, one or more candidate physiological, metabolic, molecular and/or biologic parameters that may indicate an abnormal or disease phenotype condition within the region of interest;
    analyzing, in a subvolume analysis engine, each of the image segments using an algorithm to determine, for each image segment, a probability function for each of the identified one or more candidate physiological, metabolic, and/or biologic parameters; and
    modeling the image segments, in the subvolume analysis engine, to form a probability map from the analysis of each of the image segments, the probability map providing an indication of heterogeneous distributions of the one or more candidate physiological, metabolic, and/or biological parameters for each of the image segments of the medical image data and analyzing the resulting model to identify the abnormal or disease phenotype condition within the region of interest by determining, for the medical image data, an abnormal or disease phenotype metric from the model and comparing the abnormal or disease phenotype metric with other obtained medical image data, where the identification produces a diagnostic determination of the region of interest, a prognostic determination of the target tissue, or a predictive determination of the target tissue.

2. The method of claim 1, further comprising automatically applying the diagnostic determination, prognostic determination, or predictive determination to a target tissue treatment.

3. The method of claim 2, wherein the target tissue is a tumor and wherein the target tissue treatment is radiation therapy.

4. The method of claim 1, wherein the algorithm is a fuzzy logic algorithm, a genetic algorithm or Gaussian mixture model.

5. The method of claim 1, wherein the image segments are voxels or groups of voxels.

6. The method of claim 1, wherein the one or more physiological, metabolic, molecular and/or biologic parameters include but not limit to regional cerebral blood volume (rCBV), a volume transfer coefficient ($K^{trans}$), diffusion coefficient and/or fluorodeoxyglucose (FDG) uptake.

7. The method of claim 1, wherein the medical image data is magnetic resonance image (MRI) data, positron emission tomography (PET) image data or single photon emission computed tomography (SPECT) image data.

8. The method of claim 1, wherein analyzing each of the image segments comprises applying a probability density function for each of the candidate parameters for each image segment.

9. The method of claim 8, further comprising determining the probability density function for each of the candidate parameters for an image segment collected prior to treatment of the target tissue and for an image segment collected after starting treatment of the target tissue.

10. The method of claim 8, wherein the analysis comprises modeling the probability density functions using a fuzzy-c-means (FCM) clustering analysis, Gaussian mixture model and/or other discrimination analyses.

11. The method of claim 1, further comprising assigning each of the image segments to the one or more of the candidate parameters based on the analysis of the resulting model.

12. Apparatus for analyzing medical image data of a region of interest in a sample tissue, the apparatus comprising:
    a computer system having a processor executing instructions that, when executed, (i) obtain the medical image data of the region of interest, the medical image data containing image segments, and (ii) identify one or more candidate physiological, metabolic, molecular and/or biologic parameters or features that may indicate an abnormal or disease phenotype condition within the region of interest; and
    the computer system further comprising a subvolume analysis engine to (i) analyze each of the image segments using an algorithm to determine, for each image segment, a probability function for each of the identified one or more candidate physiological, metabolic, and/or biologic parameters, (ii) model the image segments, in the subvolume analysis engine to form a probability map from the analysis of each of the image segments, the probability map providing an indication of heterogeneous distributions of the one or more candidate physiological, metabolic, and/or biological parameters for each of the image segments of the medical image data, and (iii) analyze the resulting model to identify the abnormal or disease phenotype condition within the region of interest by determining, for the medical image data, an abnormal or disease phenotype metric from the model and comparing the abnormal or disease phenotype metric with other obtained medical image data, where the identification produces a diagnostic determination of the region of interest, a prognostic determination of the target tissue, or a predictive determination of the target tissue.

13. The apparatus of claim 12, wherein the subvolume analysis engine is configured to further automatically apply the diagnostic determination, prognostic determination, or predictive determination to a target tissue treatment.

14. The apparatus of claim 12, wherein the algorithm is a fuzzy logic algorithm, a genetic algorithm or Gaussian mixture model.

15. The apparatus of claim 12, wherein the image segments are voxels or groups of voxels.

16. The apparatus of claim 12, wherein the one or more physiological, metabolic, molecular and/or biologic parameters include but not limit to regional cerebral blood volume (rCBV), a volume transfer coefficient ($K^{trans}$), diffusion coefficient and/or fluorodeoxyglucose (FDG) uptake.

17. The apparatus of claim 12, wherein the medical image data is magnetic resonance image (MRI) data, positron emission tomography (PET) image data or single photon emission computed tomography (SPECT) image data.

18. The apparatus of claim 12, wherein the subvolume analysis engine is configured to apply a probability density function for each of the candidate parameters for each image segment.

19. The apparatus of claim 18, the subvolume analysis engine is configured to further determine the probability density function for each of the candidate parameters for an image segment collected prior to treatment of the target tissue and for an image segment collected after starting treatment of the target tissue.

20. The apparatus of claim 18, wherein the analysis comprises modeling the probability density functions using a fuzzy-c-means (FCM) clustering analysis, Gaussian mixture model and/or other discrimination analyses.

* * * * *